(12) United States Patent
Mori et al.

(10) Patent No.: US 8,592,540 B2
(45) Date of Patent: Nov. 26, 2013

(54) FLUORINE-CONTAINING COMPOUND, FLUORINE-CONTAINING POLYMER COMPOUND, RESIST COMPOSITION AND PATTERNING METHOD USING SAME

(75) Inventors: Kazunori Mori, Iruma-gun (JP); Yuji Hagiwara, Kawagoe (JP); Yoshimi Isono, Kawagoe (JP); Satoru Narizuka, Saitama (JP); Kazuhiko Maeda, Chiyoda-ku (JP)

(73) Assignee: Central Glass Company, Limited, Ube-shi (JP)

( * ) Notice: Subject to any disclaimer, the term of this patent is extended or adjusted under 35 U.S.C. 154(b) by 121 days.

(21) Appl. No.: 13/141,945

(22) PCT Filed: Dec. 15, 2009

(86) PCT No.: PCT/JP2009/070865
§ 371 (c)(1),
(2), (4) Date: Jun. 23, 2011

(87) PCT Pub. No.: WO2010/073934
PCT Pub. Date: Jul. 1, 2010

(65) Prior Publication Data
US 2011/0318542 A1 Dec. 29, 2011

(30) Foreign Application Priority Data
Dec. 25, 2008 (JP) ................................. 2008-329453

(51) Int. Cl.
*C08F 18/20* (2006.01)
*C08F 20/22* (2006.01)
*G03F 7/004* (2006.01)

(52) U.S. Cl.
USPC ........... 526/245; 526/243; 525/266; 525/276; 525/279; 525/289; 430/270.1; 430/913

(58) Field of Classification Search
USPC ............... 430/270.1, 913; 525/266, 276, 279, 525/289; 526/243, 245
See application file for complete search history.

(56) References Cited

U.S. PATENT DOCUMENTS

| | | | |
|---|---|---|---|
| 7,262,252 B2 * | 8/2007 | Araki et al. ................. | 525/326.2 |
| 7,468,236 B2 | 12/2008 | Watanabe et al. | |
| 7,553,589 B2 * | 6/2009 | Araki et al. ................. | 429/316 |
| 8,034,490 B2 * | 10/2011 | Araki et al. ................. | 429/316 |
| 2005/0084231 A1 * | 4/2005 | Araki et al. ................. | 385/147 |
| 2007/0099114 A1 | 5/2007 | Watanabe et al. | |
| 2007/0179309 A1 | 8/2007 | Hasegawa et al. | |
| 2008/0311507 A1 | 12/2008 | Isono et al. | |
| 2009/0061353 A1 | 3/2009 | Isono et al. | |
| 2010/0246014 A1 * | 9/2010 | Asahi et al. ................. | 359/585 |

FOREIGN PATENT DOCUMENTS

| | | | |
|---|---|---|---|
| JP | 1-242551 A | | 9/1989 |
| JP | 07117188 A | * | 5/1995 |
| JP | 10-161313 A | | 6/1998 |
| JP | 2000-89463 A | | 3/2000 |
| JP | 2004-175740 A | | 6/2004 |
| JP | 2007-86514 A | | 4/2007 |
| JP | 2007-108451 A | | 4/2007 |
| JP | 2007-119678 A | | 5/2007 |
| JP | 2007-204385 A | | 8/2007 |
| JP | 2008-94835 A | | 4/2008 |
| JP | 2009-74085 A | | 4/2009 |
| TW | 2007-34820 A | | 9/2007 |

OTHER PUBLICATIONS

Machine translation of JP 07-117188 (no date).*
Corresponding International Search Report (Form PCT/ISA/210) dated Feb. 23, 2010 with English Translation including Form PCT/ISA/237 (Six(6) pages).
E. Ann Hallinan et al., "2, 2-Difluoro-3-Hydroxyesters by Reformatskii Reaction", Tetrahedron Letters, 1984, pp. 2301-2302, vol. 25, No. 22, Pergamon Press Ltd.
Taiwanese Office Action dated Nov. 22, 2012 (three (3) pages).

* cited by examiner

*Primary Examiner* — Amanda C. Walke
(74) *Attorney, Agent, or Firm* — Crowell & Moring LLP

(57) ABSTRACT

There is disclosed a fluorine-containing polymer compound comprising a repeating unit (a) of the following general formula (2) and having a weight-average molecular weight of 1000 to 1000000

[Chem. 69]

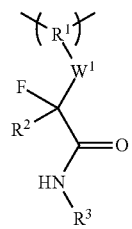

(2)

where $R^1$ represents a polymerizable double bond-containing group; $R^2$ represents a fluorine atom or a fluorine-containing alkyl group; $R^3$ represents a hydrogen atom, an acid labile group, a cross-linking site or the other monovalent organic group; and $W^1$ represents a linking moiety.

When the fluorine-containing polymer compound is used in a resist compound for pattern formation by high energy radiation of 300 nm or less wavelength or electron beam radiation, it is possible to form a resist pattern with a good rectangular profile.

19 Claims, No Drawings

FLUORINE-CONTAINING COMPOUND, FLUORINE-CONTAINING POLYMER COMPOUND, RESIST COMPOSITION AND PATTERNING METHOD USING SAME

TECHNICAL FIELD

The present invention relates to a novel fluorine-containing compound, a fluorine-containing polymer compound derived from the novel fluorine-containing compound, a resist composition using the fluorine-containing polymer compound, and a pattern formation method using the resist composition.

BACKGROUND ART

With the recent development of digital devices such as computers, it has become common to handle an enormous amount of computing data and two- and three-dimensional image data. There is a need to provide large-capacity high-speed memories and high-performance microprocessors for quick processing of such enormous information. Further, the processing power required of the digital devices is estimated to increase more and more as broadband spreads with the development of network systems such as the Internet.

In order to attain this need, various devices and equipment e.g. semiconductor devices are required to achieve higher density and higher integration. In particular, the requirements for photolithography techniques for fine patterning of the semiconductor devices are becoming more stringent year by year. For example, a photolithography process using ArF excimer laser radiation (wavelength: 193 nm) has been put into use in response to the requirement for patterning with a minimum line width of 0.13 μm or less for production of 1-Gbit or higher-capacity DRAMs. Further, the development of a photolithography process using 13.5-nm wavelength extreme ultraviolet (EUV) radiation has been pursued for finer patterning.

Although novolac resins and polyvinylphenol resins are conventionally used in resist compositions, these resins cannot be used in the above wavelength ranges because of too high light absorption. There have thus been examined, as alternative resist resins, acrylic resins (see e.g. Patent Document 1) and cycloolefin resin resins (see e.g. Patent Document 2).

In the case of forming a pattern by the use of a photoresist composition, it is preferable to utilize an aqueous tetramethylammonium hydroxide (TMAH) solution, rather than an organic solvent, as a developer in consideration of environmental issues. Herein, a phenolic hydroxyl group, a carboxyl group and a hexafluoroisopropanol group are each known as a functional group soluble in the aqueous TMAH solution, i.e., developable with the aqueous TMAH solution. For use of a photoresist composition by exposure at an ArF laser wavelength (193 nm) or a $F_2$ laser wavelength (157 nm), the introduction of a carboxyl group or a hexafluoroisopropanol group to a resist resin has mainly been examined in view of the fact that an aromatic ring has a strong wide absorption band in these wavelength ranges. When the resist resin has a hexafluoroisopropanol functional group, the resulting resist composition shows good developability and substrate adhesion properties and attains a relatively favorable pattern profile in fine patterning process. However, special specific synthesis techniques are required for the synthesis of such a hexafluoroisopropanol-containing resin. On the other hand, when the resist resin has a carboxyl functional group, it is difficult to form a desired pattern by the use of such a carboxyl-containing resist resin as the carboxyl-containing resin is swelled in the TMAH solution (see Patent Document 3).

There have further been known, as carboxylic acid compounds with α-position fluorine, 2-fluoro-phenylacetic acid and ester thereof (see Patent Document 4) and ethyl-2,2-difluoro-3-hydroxy-3-phenylpropionic acid (see Non-Patent Document 1).

PRIOR ART DOCUMENTS

Patent Documents

Patent Document 1: Japanese Laid-Open Patent Publication No. 10-161313
Patent Document 2: Japanese Laid-Open Patent Publication No. 2000-89463
Patent Document 3: Japanese Laid-Open Patent Publication No. 2007-86514
Patent Document 4: Japanese Laid-Open Patent Publication No. 1-242551

Non-Patent Documents

Non-Patent Document 1: Tetrahedron Letters, Vol. 25, No. 22, pp 2301-2302, 1984

DISCLOSURE OF THE INVENTION

It is an object of the present invention to provide a resist composition for pattern formation by exposure to high energy radiation of 300 nm or less wavelength or electron beam radiation, wherein the resist composition contains a polymer compound formed with a novel structure so as to form a pattern with a good rectangular profile without impairing transparency by exposure. It is also an object of the present invention to provide a useful monomer for the formation of such a novel structured polymer compound.

The present inventors have made extensive researches on the solubility of various functional groups in an aqueous tetramethylammonium hydroxide (TMAH) solution used as a general-purpose developer to develop a patterned resist film. As a result of such extensive researches, the present inventors have found that, although it has not been known that a carbamoyl group makes an insoluble resin soluble in the presence of an acid as in the case of a carboxyl group, the introduction of a fluorine atom to α-position of the carbamoyl group makes it possible to impart strong acidity to the carbamoyl group and thereby increase the solubility of the resin whose repeating unit contains such a carbamoyl group and also makes it possible that the film of the carbamoyl-containing resin can be dissolved in the TMAH solution without causing swelling and can form a pattern with a rectangular profile as desired. The present inventors have also found that the repeating unit of the resin combines a strongly acidic carbamoyl hydrogen atom with a cross-linking site by the substitution of a hydrogen atom of the carbamoyl group with a neutral hydroxyl-containing alkyl group etc. so that the resin becomes highly soluble and suitable for a negative resist material and that the repeating unit of the resin combines a strongly acidic carbamoyl hydrogen atom with an acid labile site by the substitution of a hydrogen atom of the carbamoyl group with an acid labile group so that the resin becomes highly soluble and suitable for a positive resist material. The present inventors have further found a novel polymerizable fluorine-containing compound useful for the introduction of the fluorine atom to α-position of the carbamoyl group of the fluorine-containing polymer compound in the resist composition according to the present invention.

Namely, the present invention includes the following aspects [1] to [19].

[Aspect 1]

A fluorine-containing unsaturated carboxylic acid amide of the following general formula (1)

[Chem. 1]

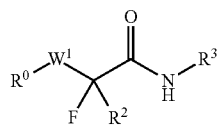

(1)

where $R^0$ represents any of polymerizable double bond-containing groups of the following formulas:

[Chem. 2]

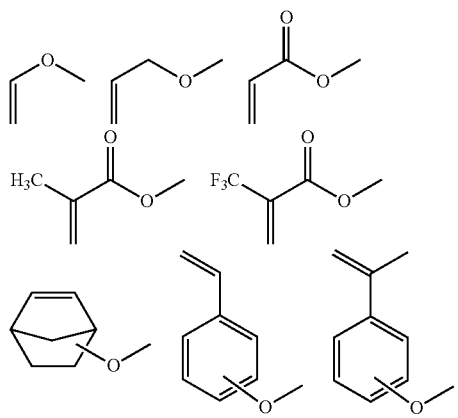

$R^2$ represents a fluorine atom or a fluorine-containing alkyl group;

$R^3$ represents a hydrogen atom, a substituted or unsubstituted $C_1$-$C_{20}$ straight, branched or cyclic alkyl group or a substituted or unsubstituted $C_3$-$C_{20}$ aryl group, each of carbon atoms of the alkyl group or the aryl group may be replaced by a carbonyl group, an oxygen atom, a sulfur atom or a silicon atom, each of hydrogen atoms of the alkyl group or the aryl group may be replaced by a halogen atom;

$W^1$ represents a divalent linking moiety constituted by combination of one or two or more organic groups each selected from the group consisting of a single bond, a substituted or unsubstituted methylene group, a divalent alicyclic hydrocarbon group, a divalent aromatic hydrocarbon group, an ether group, a carbonyl group, an ester group, an oxocarbonyl group, a thioether group, an amide group, a sulfonamide group, an urethane group, an urea group, a divalent alicyclic hydrocarbon group and a divalent aromatic hydrocarbon group; when the linking moiety contains a plurality of organic groups, the organic groups can be of the same kind; an arbitrary number of hydrogen atoms bonded to any carbon atom of the linking moiety may be substituted with a fluorine atom; and carbon atoms of the linking moiety may form a ring with a substituent.

[Aspect 2]

The fluorine-containing unsaturated carboxylic acid amide according to Aspect 1, wherein $R^2$ is a fluorine atom.

[Aspect 3]

The fluorine-containing unsaturated carboxylic acid amide according to Aspect 1 or 2, wherein $R^3$ is a hydrogen atom.

[Aspect 4]

The fluorine-containing unsaturated carboxylic acid amide according to Aspect 1 or 2, wherein $R^3$ is an acid labile group.

[Aspect 5]

The fluorine-containing unsaturated carboxylic acid amide according to Aspect 1 or 2, wherein $R^3$ is a neutral alkoxyl-containing group.

[Aspect 6]

A fluorine-containing polymer compound, comprising a repeating unit (a) of the following general formula (2) and having a weight-average molecular weight of 1000 to 1000000

[Chem. 3]

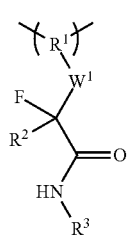

(2)

where $R^1$ represents a group formed by cleavage of a polymerizable double bond of $R^0$ defined in the general formula (1); and $R^2$, $R^3$ and $W^1$ are the same as defined in the general formula (1).

[Aspect 7]

The fluorine-containing polymer compound according to Aspect 6, wherein $R^2$ is a fluorine atom.

[Aspect 8]

The fluorine-containing polymer compound according to Aspect 6 or 7, wherein $R^3$ is a hydrogen atom.

[Aspect 9]

The fluorine-containing polymer compound according to Aspect 6 or 7, wherein $R^3$ is an acid labile group.

[Aspect 10]

The fluorine-containing polymer compound according to Aspect 6 or 7, wherein $R^3$ is a neutral alkoxyl-containing group.

[Aspect 11]

The fluorine-containing polymer compound according to any one of Aspects 6 to 10, further comprising a repeating unit (b) formed by cleavage of a polymerizable double bond of a copolymerizable monomer selected from the group consisting of acrylic esters, fluorine-containing acrylic esters, methacrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylic amides, methacrylic amides, vinyl esters, allyl esters, olefins, fluorine-containing olefins, norbornene compounds, fluorine-containing norbornene compounds, sulfur dioxide and vinyl silanes.

[Aspect 12]

The fluorine-containing polymer compound according Aspect 11, wherein the repeating unit (b) has a lactone ring.

[Aspect 13]

A resist composition, comprising at least the fluorine-containing polymer compound according to any one of Aspects 6 to 12 and a solvent.

[Aspect 14]

A chemically amplified resist composition, comprising at least the fluorine-containing polymer compound according to any one of Aspects 6 to 12, a photoacid generator and a solvent.

[Aspect 15]

A chemically amplified positive resist composition, comprising at least the fluorine-containing polymer compound according to any one of Aspects 6 to 12, a photoacid generator and a solvent.

[Aspect 16]

A chemically amplified negative resist composition, comprising at least the fluorine-containing polymer compound according to any one of Aspects 6 to 12, a photoacid generator, a cross-linking agent and a solvent.

[Aspect 17]

A pattern formation method, comprising at least: applying a film of the resist composition according to any one of Aspects 13 to 16 to a substrate; heat-treating the substrate with the film of the resist composition being applied; exposing the film of the resist composition to high energy radiation of 300 nm or less wavelength or electron beam radiation through a photomask; heat-treating the exposed film of the resist composition; and developing the heat-treated, exposed film of the resist composition with a developer.

[Aspect 18]

The pattern formation method according to Aspect 17, wherein the high energy radiation is either near-ultraviolet radiation, vacuum ultraviolet radiation (VUV), extreme ultraviolet radiation (EUV) or soft X-ray radiation.

[Aspect 19]

An electronic device, comprising a pattern formed by the pattern formation method according to Aspect 17 or 18.

In the present specification and claims, the term "alkyl group" denotes a straight, branched or cyclic alkyl group. The cyclic alkyl group is also classified as an "alicyclic group" or "alicyclic hydrocarbon group".

The term "lower" means that a group such as alkyl group to which the term is attached is of 1 to 4 carbon atoms. The term "lower cyclic alkyl group" however denotes a $C_3$-$C_{10}$ alkyl group that has a ring structure and may have a lower alkyl group as a substituent. As such an alkyl group, there can be used methyl, ethyl, propyl, butyl, cyclopentyl, cyclohexyl, norbornyl, adamantyl, trifluoromethyl, 2,2,2-trifluoroethyl, 1-(trifluoromethyl)ethyl or 3,3,3-trifluoropropyl.

In the case of referring to a compound having isomers, all possible isomers are included by one compound name and structural formula unless otherwise specified. The term "halogen" denotes fluorine, chlorine, bromine or iodine.

DETAILED DESCRIPTION

The resist composition according to the present invention has the advantage of, when a film of the resist composition is irradiated with high energy radiation of 300 nm or less wavelength or electron beam radiation, changing its solubility in an aqueous TMAH solution and forming a pattern with a good rectangular profile. The fluorine-containing polymer compound of the general formula (2) can suitably be used as a base resin of the resist composition according to the present invention. (Herein, the term "base resin" denotes a positive or negative resist resin that causes changes in solubility by exposure. The same applies for the following description.) Further, the fluorine-containing compound of the general formula (1) has the advantage of introducing an acid labile group or a cross-linking site easily and efficiently into the base resin of the resist composition according to the present invention.

Hereinafter, the respective components of the present invention will be described in detail below. The present invention is not however limited to the following embodiments. Various changes and modifications of the following embodiments can be made, based on general knowledge of those skilled in the art, without departing from the scope of the present invention.

The fluorine-containing polymer compound of the present invention has a repeating unit (a) of the general formula (2) formed by cleavage of a polymerizable double bond of the fluorine-containing compound of the general formula (1) and, more specifically, can be in the form of a homopolymer consisting of the repeating unit (a) or a copolymer containing not only the repeating unit (a) but also any other repeating unit formed by cleavage of a polymerizable double bond of another monomer.

[Fluorine-Containing Unsaturated Carboxylic Acid Amide]

In the fluorine-containing unsaturated carboxylic acid amide of the general formula (1), $R^2$ is a fluorine atom or a fluorine-containing alkyl group.

[Chem. 4]

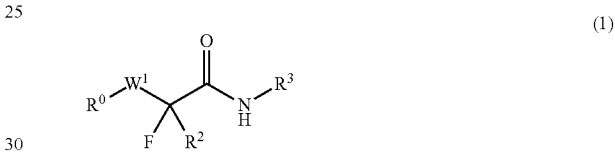

(1)

Although the fluorine-containing alkyl group is not particularly limited, it is preferable that the fluorine-containing alkyl group is of 1 to 12 carbon atoms, more preferably 1 to 3 carbon atoms. Examples of the fluorine-containing alkyl group are trifluoromethyl, pentafluoroethyl, 2,2,2-trifluoroethyl, n-heptafluoropropyl, 2,2,3,3,3-hentafluoropropyl, 3,3,3-trifluoropropyl and hexafluoropropyl. Among others, a fluorine atom or a trifluoromethyl group is particularly preferred as $R^2$.

Although there can be used as $R^0$ any polymerizable double bond-containing groups, $R^0$ is preferably either one of polymerizable double bond-containing groups of the following formulas.

[Chem. 5]

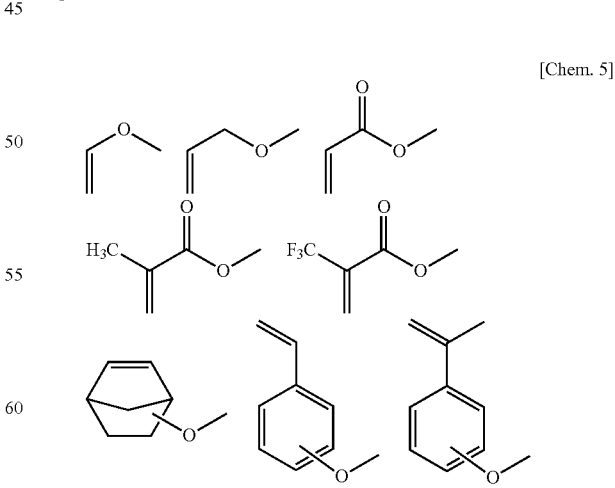

Among others, an acryloxy group, a methacryloxy group, a trifluoromethacryloxy group and an allyloxy group are particularly preferred.

Further, $W^1$ is a divalent linking moiety whose main skeleton is constituted by combination of one or two or more each selected from the group consisting of a single bond, a substituted or unsubstituted methylene group, a divalent alicyclic hydrocarbon group, a divalent aromatic hydrocarbon group, a divalent heterocyclic group, an ether group, a carbonyl group, an ester group, an oxocarbonyl group, a thioether group, an amide group, a sulfonamide group, an urethane group and an urea group. When the linking moiety contains a plurality of groups, these groups can be of the same kind. An arbitrary number of hydrogen atoms bonded to any carbon atom of the linking moiety may be substituted with a fluorine atom. Carbon atoms of the linking moiety may form a ring with a substituent.

The substituted methylene group as the constituent of the main skeleton of the linking moiety $W^1$ is represented by the following general formula (3):

$$—CR^4R^5— \quad (3)$$

wherein $R^4$ and $R^5$ each represents a monovalent group.

Although the monovalent groups $R^4$ and $R^5$ of the substituted methylene group are not particularly limited, each of the monovalent group $R^4$ and $R^5$ is a hydrogen atom, a halogen atom, a hydroxyl group or a $C_1$-$C_{30}$ monovalent group selected from the group consisting of a substituted or unsubstituted alkyl group, a substituted or unsubstituted alicyclic hydrocarbon group, an alkoxyl group, a substituted or unsubstituted aryl group and a substituted or unsubstituted condensed polycyclic aromatic group. These monovalent groups $R^4$ and $R^5$ may each contain a fluorine atom, an oxygen atom, a sulfur atom, a nitrogen atom or a carbon-carbon double bond, may be of the same kind or different kinds, and may form a ring structure, preferably an alicyclic hydrocarbon ring structure, with any atom in the molecule. The monovelent organic groups $R^4$ and $R^5$ can be exemplified as follows.

The acyclic alkyl group as $R^4$, $R^5$ is of 1 to 30 carbon atoms, preferably 1 to 12 carbon atoms. Example of the acyclic alkyl group are methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl and i-propyl.

The substituted acyclic alkyl group as $R^4$, $R^5$ is a group in which one or two or more hydrogen atoms of the above alkyl group is substituted with a $C_1$-$C_4$ alkoxyl group, a halogen atom, an acyl group, acyloxy group, a cyano group, a hydroxyl group, a carboxy group, alkoxycarbonyl group or a nitro group. Among others, fluoroalkyl groups each having a fluorine atom as a substituent are preferred. Examples of the fluoroalkyl group are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl.

The alicyclic hydrocarbon group as $R^4$, $R^5$ or formed by $R^4$ and $R^5$ together with carbon bonded thereto can be monocyclic or polycyclic. Examples of the alicyclic hydrocarbon group are those of 3 or more carbon atoms each having a monocyclo, bicyclo, tricycle or tetracyclo structure. The alicyclic hydrocarbon group preferably has 3 to 30 carbon atoms, more preferably 3 to 25 carbon atoms, and may have a substituent.

The monocyclic hydrocarbon group is preferably of 3 to 12 ring carbons, more preferably 3 to 7 ring carbons. Preferred examples of the monocyclic hydrocarbon groups are cyclopropyl, cyclobutyl, cyclohexyl, cycloheptyl, cyclooctyl, cyclodecanyl, cyclododecanyl and 4-tert-butylcyclohexyl. The polycyclic hydrocarbon group is preferably of 7 to 15 ring carbons. Preferred examples of the polycyclic hydrocarbon group are adamantyl, noradamantyl, decalin residue, tricyclodecanyl, tetracyclododecanyl, norbornyl and cedrol. Further, the alicyclic hydrocarbon group can be a spiro ring, preferably a $C_3$-$C_6$ spiro ring. Among others, particularly preferred are adamantyl, decalin residue, norbornyl, cedrol, cyclohexyl, cycloheptyl, cyclooctyl, cyclodecanyl, cyclododecanyl and tricyclodecanyl. One or two or more hydrogen atoms on the ring carbons of the above organic group, or one or two or more hydrogen atoms of the above linking moiety, may be each independently substituted with a substituent such as a $C_1$-$C_{30}$ alkyl or substituted alkyl group, a hydroxyl group, an alkoxy group, a carboxyl group or an alkoxycarbonyl group. One or two or more hydrogen atoms of this substituent group may further be substituted with fluorine or trifluoromethyl.

Herein, a lower alkyl group is preferred as the $C_1$-$C_{30}$ alkyl group. Particularly preferred is an alkyl group selected from the group consisting of methyl, ethyl, propyl and isopropyl. Further, a hydroxyl group, a halogen atom or an alkoxyl group is usable as the substituent of the alkyl group. As the alkoxyl substituent group, there can be used those of 1 to 4 carbon atoms, such as methoxy, ethoxy, propoxy and butoxy. There can be used methoxycarbonyl, ethoxycarbonyl and isopropoxycarbonyl as the alkoxycarbonyl substituent group.

The alkoxy group as $R^4$, $R^5$ is of 1 to 4 carbon atoms, such as methoxy, ethoxy, propoxy or butoxy.

The substituted or unsubstituted aryl group as $R^4$, $R^5$ is of 1 to 30 carbon atoms and, when it is monocyclic, is preferably of 3 to 12 ring carbons, more preferably 3 to 6 ring carbons. Examples of the aryl group are phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

The substituted or unsubstituted $C_1$-$C_{30}$ condensed polycyclic aromatic group as $R^4$, $R^5$ is a monovalent organic group obtained by elimination of one hydrogen atom from pentalene, indene, naphthalene, azulene, heptalene, biphenylene, indacene, acenaphthylene, fluororene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene or the like. One or two or more hydrogen atoms of the above condensed aromatic group may preferably be substituted with a fluorine atom or a $C_1$-$C_4$ alkyl or fluoroalkyl group.

There can be used monocyclic or polycyclic heterocyclic groups of 3 to 25 ring atoms, such as pyridyl, furil, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One or two or more hydrogen atoms on any of the ring atoms of the heterocyclic group may be substituted with an alkyl, alicyclic hydrocarbon, aryl or heterocyclic group. Among others, preferred are those having a monocyclic or polycyclic ether ring or a lactone ring as exemplified below.

[Chem. 6]

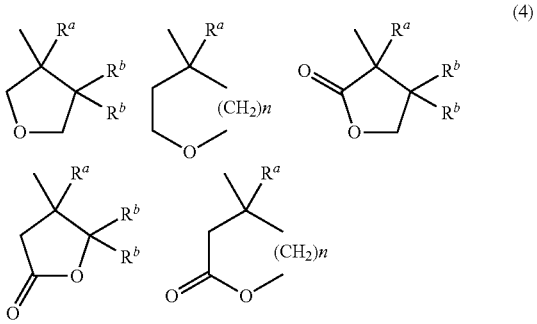

(4)

In the above formulas, $R^a$ and $R^b$ each independently represent a hydrogen atom or a $C_1$-$C_4$ alkyl group; and n represents an integer of 2 to 4.

The divalent alicyclic hydrocarbon group as the constituent of the main skeleton of the linking moiety $W^1$ can be either monocyclic or polycyclic. Examples of the alicyclic hydrocarbon group are those of 3 or more carbon atoms each having a monocyclo, bicyclo, tricycle or tetracyclo structure. The alicyclic hydrocarbon group preferably has 3 to 30 carbon atoms, more preferably 3 to 25 carbon atoms, and may have a substituent.

The monocyclic hydrocarbon group is preferably of 3 to 12 ring carbons, more preferably 3 to 7 ring carbons. Preferred examples of the monocyclic hydrocarbon group are cyclopropyl, cyclobutyl, cyclopentyl, cyclohexyl, cycloheptyl, cyclooctyl, cyclodecanyl, cyclododecanyl, and 4-tert-butyl-cyclohexyl. The polycyclic hydrocarbon group is preferably of 7 to 15 ring carbons. Preferred examples of the polycyclic hydrocarbon group are adamantyl, noradamantyl, decalin residue, tricyclodecanyl, tetracyclododecanyl, norbornyl and cedrol. The alicyclic hydrocarbon group can be a spiro ring, preferably a $C_3$-$C_6$ Spiro ring. Preferred examples of the spiro ring are adamantyl, decalin residue, norbornyl, cedrol, cyclohexyl, cycloheptyl, cyclooctyl, cyclodecanyl and tricyclodecanyl. One or two or more hydrogen atoms on the ring carbons of the above organic group, or one or two or more hydrogen atoms of the above linking moiety, may be each independently substituted with a substituent such as a $C_1$-$C_{30}$ alkyl or substituted alkyl group, a hydroxyl group, an alkoxy group, a carboxyl group or an alkoxycarbonyl group as explained for $R^4$, $R^5$. One or two or more hydrogen atoms of this substituent group may further be substituted with fluorine or trifluoromethyl.

As the $C_1$-$C_{30}$ alkyl group, a lower alkyl group is preferred. Particularly preferred is an alkyl group selected from the group consisting of methyl, ethyl, propyl and isopropyl. Further, a hydroxyl group, a halogen atom or an alkoxyl group is usable as the substituent of the alkyl group. As the alkoxyl substituent group, there can be used those having 1 to 4 carbon atoms, such as methoxy, ethoxy, propoxy and butoxy. There can be used methoxycarbonyl, ethoxycarbonyl and isopropoxycarbonyl as the alkoxycarbonyl substituent group.

The divalent aromatic hydrocarbon group as the constituent of the main skeleton of the linking moiety $W^1$ is of 1 to 30 carbon atoms and, when it is monocyclic, is preferably of 3 to 12 ring carbons, more preferably 3 to 6 ring carbons. Examples of the divalent aromatic hydrocarbon group as $W^1$ are divalent organic groups obtained by elimination of two hydrogen atoms from benzene, biphenyl, terphenyl, toluene, phenol, anisole, mesitylene, cumene, 2,3-xylylene, 2,4-xylylene, 2,5-xylylene, 2,6-xylylene, 3,4-xylylene, 3,5-xylylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene and the like.

The substituted or unsubstituted condensed polycyclic aromatic group as the constituent of the main skeleton of the linking moiety $W^1$ is preferably of carbon atoms 1 to 30. Examples of the substituted or unsubstituted condensed polycyclic aromatic group as $W^1$ are divalent organic groups obtained by elimination of two hydrogen atoms from pentalene, indene, naphthalene, azulene, heptalene, biphenylene, indacene, acenaphthylene, fluororene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. One or two or more hydrogen atoms of the condensed-ring aromatic group may be substituted with a fluorine atom or a $C_1$-$C_4$ alkyl or fluoroalkyl group.

The heterocyclic group as the constituent of the main skeleton of the linking moiety $W^1$ can be monocyclic or polycyclic. Examples of the monocyclic or polycyclic heterocyclic group are divalent organic groups obtained by elimination of two hydrogen atoms from pyridine, furan, thienine, pyranine, thianthrene, pyrazon, isothiazone, isooxazone, pyrazine, pyrimidine, pyridazine, tetrahydropyranine, tetrahydrofuranine, tetrahydrothiopyranine, tetrahyrothiofuran and the like. One or two or more hydrogen atoms on any ring atom of the monocyclic or polycyclic heterocyclic group may be substituted with an alkyl (preferably lower alkyl) group, an alicyclic hydrocarbon group, an aryl group or a heterocyclic group. Among others, preferred are monocyclic or polycyclic ether ring groups as exemplified as follows.

[Chem. 7]

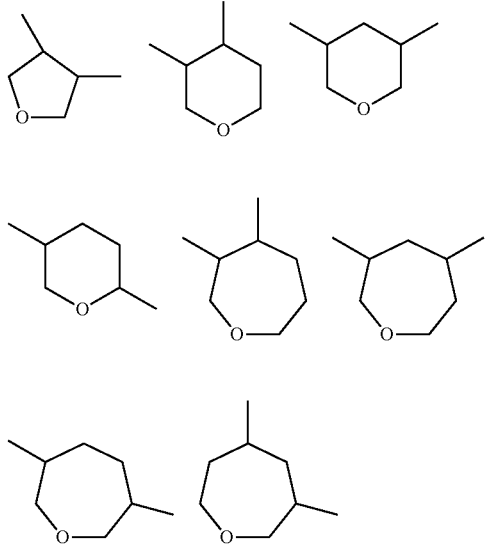

As the linking moiety $W^1$, the substituted methylene group of the general formula (3) is most preferred. Preferred examples of the substituted methylene group of the general formula (3) are indicated as follows. In each chemical formula, the O and C represent oxygen and carbon atoms adjacent to the substituted methylene group.

[Chem. 8]

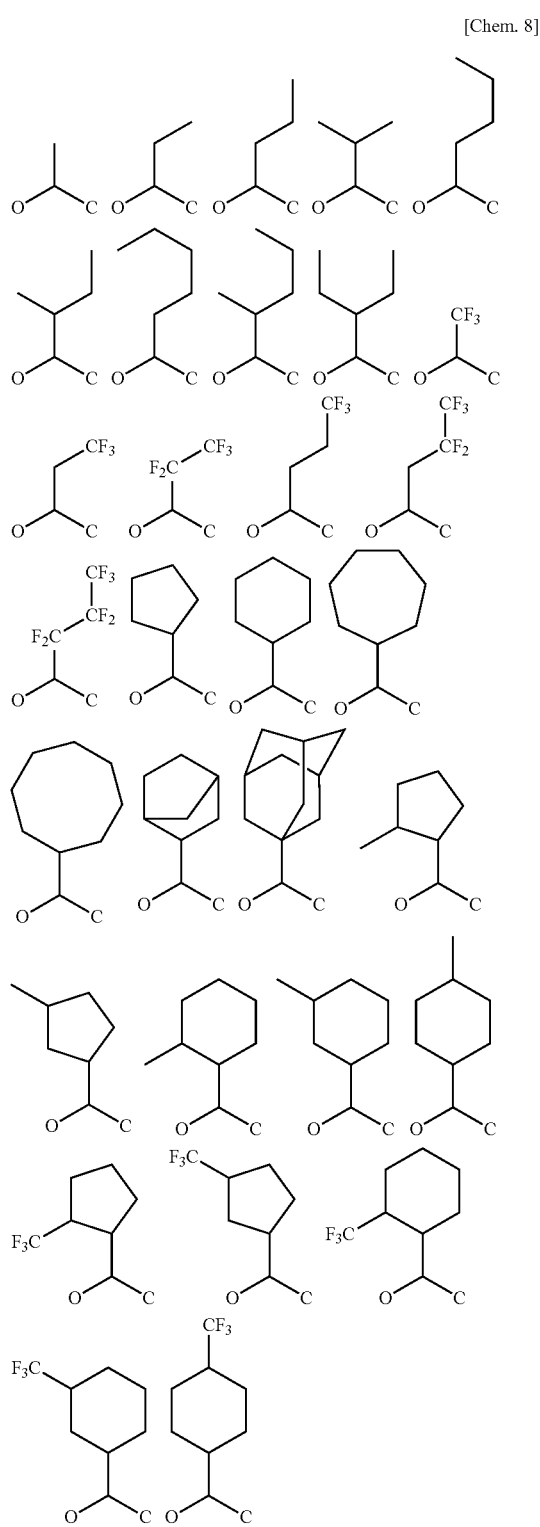

[Chem. 9]

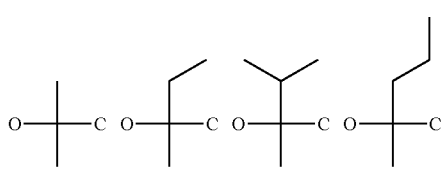

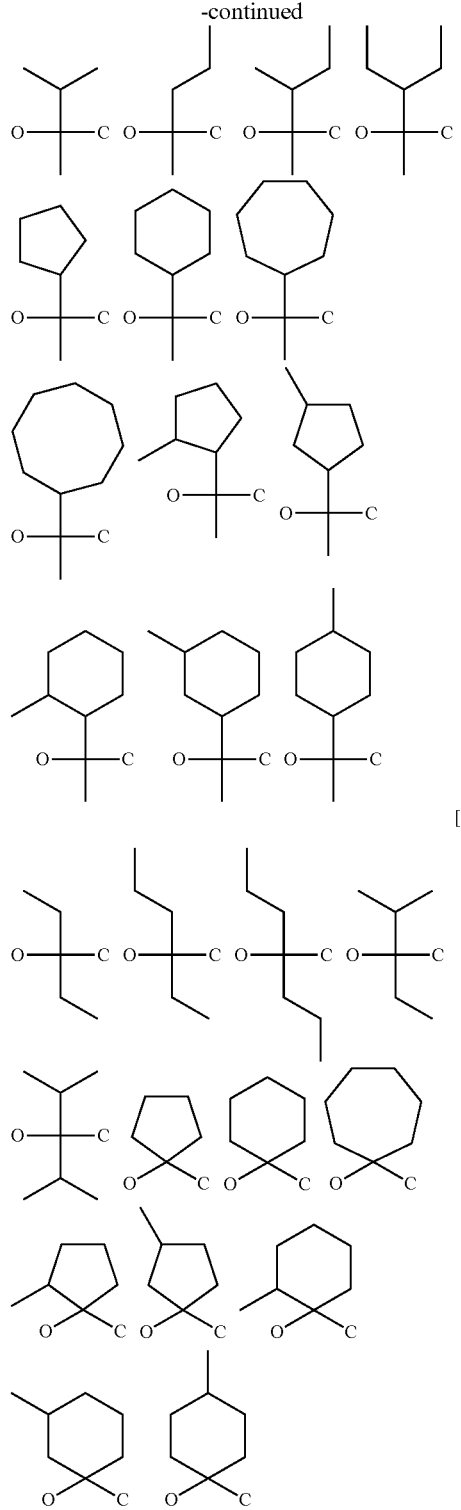

[Chem. 10]

In the fluorine-containing unsaturated carboxylic acid amide of the general formula (1), $R^3$ is a monovalent organic group selected depending on the purpose of use of the fluorine-containing unsaturated carboxylic acid amide and the polymer compound derived therefrom. In the homopolymer or copolymer of the fluorine-containing unsaturated carboxylic acid amide, which has the repeating unit (a) of the general formula (2), $R^3$ is (i) a hydrogen atom, (ii) an acid labile group capable of being eliminated from the polymer in the presence of an acid generated from an acid generator by light irradiation such that the polymer, which has been insoluble in an aqueous alkali solution before the light irradiation, can be made soluble in the aqueous alkali solution, (iii) a neutral hydroxyl-containing group that contains a neutral hydroxyl group capable of reacting with a cross-linking agent in the presence of an acid generated from an acid generator by light irradiation such that the polymer, which has been soluble in an aqueous alkali solution, can be made insoluble or difficult to solve in the aqueous alkali solution, or (iv) any organic group other than the acid labile group or neutral hydroxyl-containing group. When the polymer compound has a hydrogen atom as one $R^3$ and an organic group (iv) as another $R^3$, there still exists acidic amide hydrogen to control, especially promote, the solubility of the polymer in the aqueous alkali solution.

The purpose for introducing the acid labile group into the fluorine-containing polymer compound used as the base resin of the resist composition is to, by the action of the acid labile group, develop not only the positive sensitivity of the resist composition as well as the solubility of the resist composition in the aqueous alkali solution after exposure to high energy radiation of 300 nm or less wavelength, such as excimer laser radiation classified as near ultraviolet radiation, far ultraviolet radiation or extreme ultraviolet radiation, soft X-ray radiation or X-ray radiation, or electron beam radiation. It is possible, by changing the kind of the acid labile group and the ratio of the acid labile group to the stable group (i.e. the group whose end is not acid labile), to vary and control the polarity of the end of the polymer compound and thereby optimize the properties of the polymer compound, such as solubility in solvent, applicability to substrate, surface tension, dispersibility of acid generator and acid dispersion speed.

The acid labile group (ii) as $R^3$ is an organic group represented by any of the following general formulas (d) to (h).

$$R^6\text{—O—C(=O)—} \qquad (d)$$

In the general formula (d), $R^6$ represents a $C_1$-$C_4$ alkyl group that may have a substituent, a $C_3$-$C_{30}$ alicyclic hydrocarbon group that may have a substituent, or a $C_6$-$C_{14}$ aryl group that may have a substituent.

$$R^6\text{—O—CHR}^7\text{—} \qquad (e)$$

In the general formula (e), $R^6$ is the same as defined in the general formula (d); $R^7$ represents a hydrogen atom, a $C_1$-$C_4$ alkyl group that may have a substituent, a $C_3$-$C_{30}$ alicyclic hydrocarbon group that may have a substituent, a $C_1$-$C_6$ alkoxyl group that may have a substituent, a $C_2$-$C_4$ alkenyl group that may have a substituent, a $C_6$-$C_{14}$ aryl group that may have a substituent, or a $C_2$-$C_{20}$ aralkyl group that may have a substituent.

$$CR^8R^9R^{10}\text{—} \qquad (f)$$

In the general formula (f), $R^8$, $R^9$ and $R^{10}$ may be of the same or different kinds and each independently represent a $C_1$-$C_4$ alkyl group that may have a substituent, a $C_3$-$C_{30}$ alicyclic hydrocarbon group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent. Two of $R^8$, $R^9$ and $R^{10}$ may be bonded together to form a ring.

$$SiR^8R^9R^{10}\text{—} \qquad (f)$$

In the general formula (g), $R^8$, $R^9$ and $R^{10}$ are the same as defined in the general formula (f).

$$R^6\text{—C(=O)—} \qquad (h)$$

In the general formula (h), $R^6$ is the same as defined in the general formula (d).

In the general formulas (d) to (h), each of $R^6$, $R^7$, $R^8$, $R^9$ and $R^{10}$ are each independently a monovalent organic group as mentioned above and as will be explained below in detail. Among others, the acid labile group by any of the general formula (d), (e) and (f) is suitably usable in the resist composition for pattern formation by exposure to high energy radiation of 300 nm or less wavelength as the polymer with such an acid labile group can serve as a chemically amplified resist resin that allows elimination of the acid labile group from the polymer in the presence of an acid ($H^+$) generated from a photoacid generator by light irradiation as well as reproduction of the acid.

As mentioned above, $R^6$ represents an alkyl group, an alicyclic hydrocarbon group or an aryl group; $R^7$ is a hydrogen atom, an alkyl group, an alicyclic hydrocarbon group, an alkenyl group, an aralkyl group, an alkoxyl group or an aryl group; and $R^8$, $R^9$ and $R^{10}$ may be of the same kind or different kinds and each independently represent an alkyl group, an alicyclic hydrocarbon group, an alkenyl group, an aralkyl group or an aryl group. Two of $R^8$, $R^9$ and $R^{10}$ may be bonded together to form a ring.

Preferred examples of the alkyl group are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, boronyl, tricyclodecanyl, dicyclopentenyl, norbornaneepoxy, menthyl, isomenthyl, neomenthyl, tetracyclodecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, toluyl, cumenyl, naphthyl and anthracenyl. These organic groups may have substituents. Examples of the aralkyl group are those of 7 to 20 carbon atoms, such as benzyl, phenethyl and cumyl, each of which may have a substituent.

As the substituents of the above organic groups, there can be used a hydroxyl group, a halogen atom (preferably a fluorine atom), a nitro group, a cyano group, any of the above-mentioned alkyl and alicyclic hydrocarbon groups, alkoxy groups such as methoxy, ethoxy, hydroxyethoxy, propoxy, hydroxypropoxy, n-butoxy, isobutoxy, sec-butoxy and tert-butoxy, alkoxycarbonyl groups such as methoxycarbonyl and ethoxycarbonyl, aralkyl groups such as benzyl, phenethyl and cumyl, aralkyloxy groups, acyl groups such as formyl, acetyl, butyryl, benzoyl, cyanamyl and valeryl, acyloxy groups such as butyryloxy, any of the above-mentioned alkenyl groups, alkenyloxy groups such as vinyloxy, propenyloxy, allyloxy and butenyloxy, any of the above-mentioned aryl groups, aryloxy group such as phenoxy, and aryloxycarbonyl groups such as benzoyloxy.

Lactone groups of the following formulas (5) and (6) are also usable.

[Chem. 11]

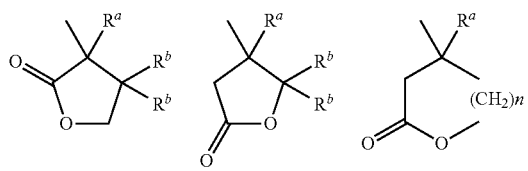
(5)

-continued

[Chem. 12]

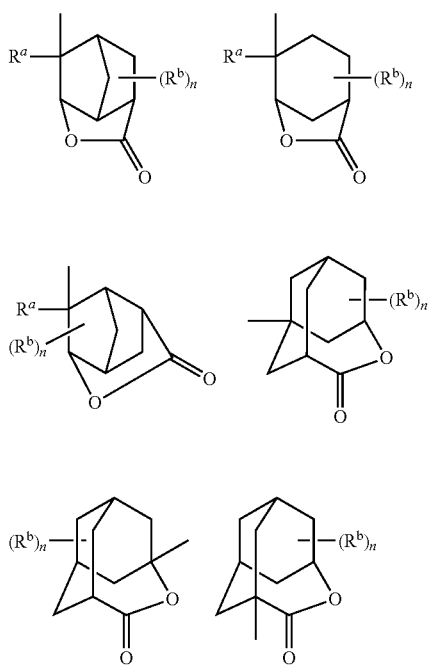

(6)

In the above formulas, $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxyl group, a carboxylic acid group, an alkyloxycarbonyl group or an alkoxy group; and n represents an integer of 1 to 4.

The following are specific examples of the acid labile group.

Specific examples of the alkoxycarbonyl group represented by the general formula (d): $R^6$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantaneoxycarbonyl.

Specific examples of the acetal group represented by the general formula (e): $R^6$—O—CHR$^7$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. An acetal group obtained by the addition of a vinyl ether to a hydroxy group is also usable.

Specific examples of the tertiary hydrocarbon group represented by the general formula (f): CR$^8$R$^9$R$^{10}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isoboronyl, 1-methyladamantyl, 1-ethyladamantyl, 1-isopropyladamantyl, 1-isopropylnorbornyl and 1-isopropyl-(4-methylcyclohexyl).

The alicyclic hydrocarbon group or the alicyclic hydrocarbon-containing acid labile group can be exemplified as follows.

[Chem. 13]

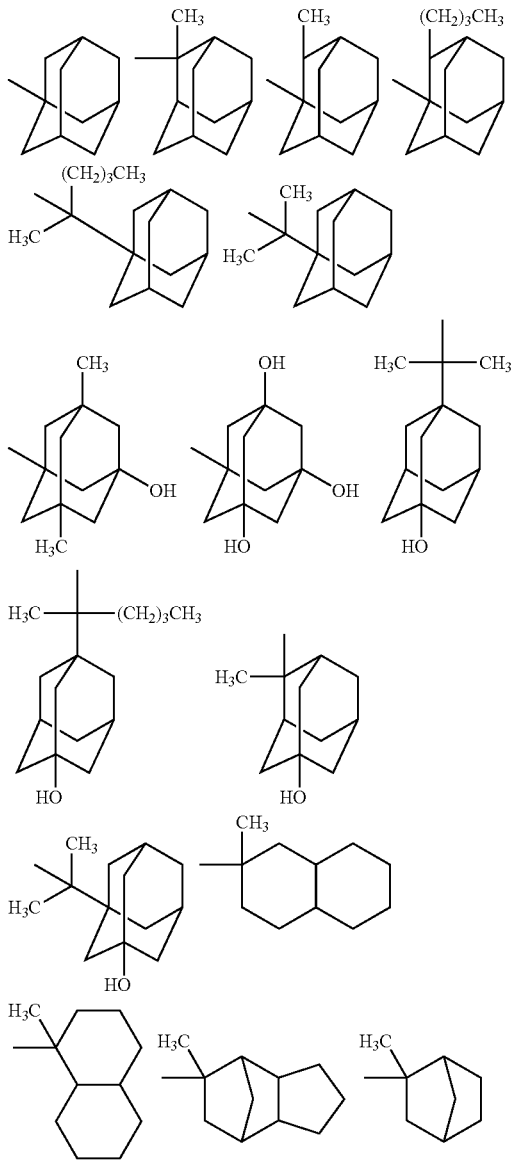

[Chem. 14]

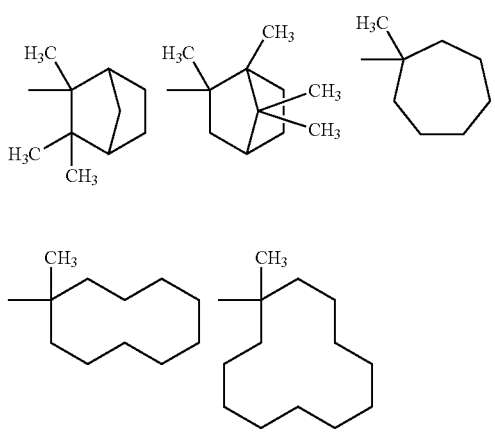

-continued

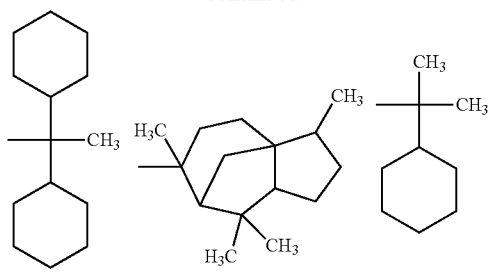

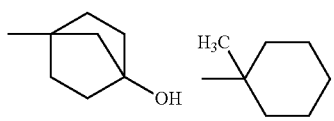

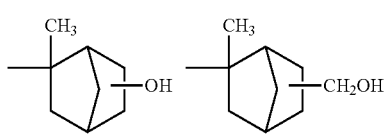

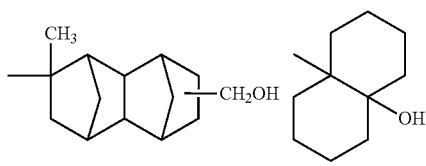

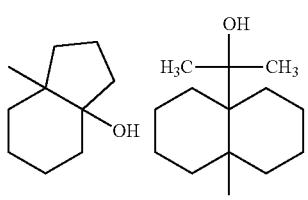

In the above formulas, methyl (CH$_3$) groups may independently be replaced with ethyl groups; and one or two or more of ring carbons may have a substituent group as mentioned above.

Specific examples of the silyl group represented by the general formula (g): SiR$^8$R$^9$R$^{10}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (h): R$^6$—C(=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. A part or all of hydrogen atoms of these acid labile groups may be substituted with fluorine.

The lactone-containing acid labile group can be exemplified as follows.

[Chem. 15]

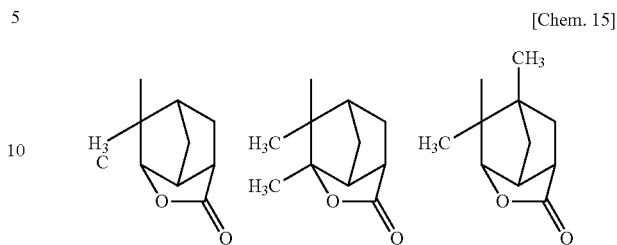

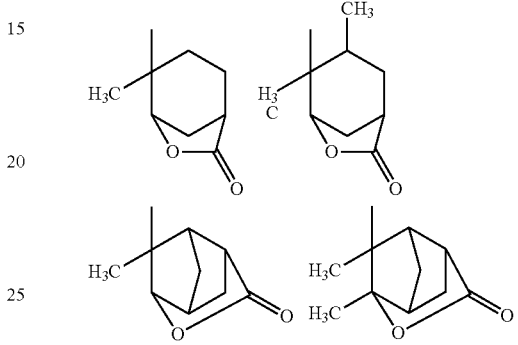

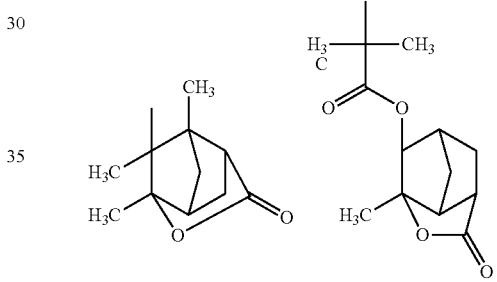

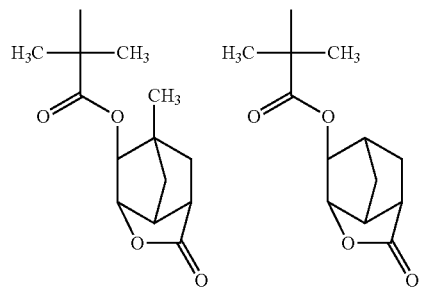

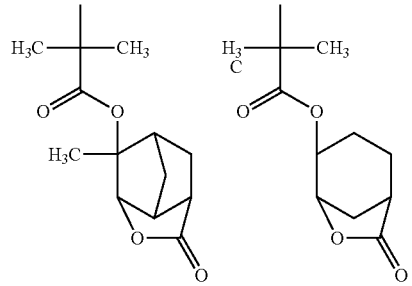

-continued

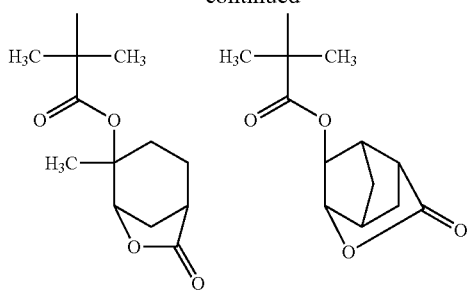

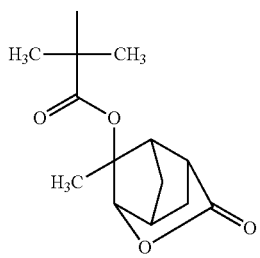

[Chem. 16]

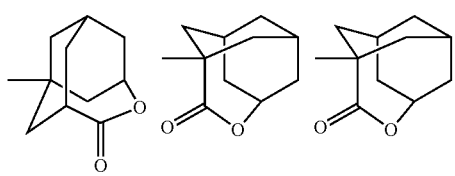

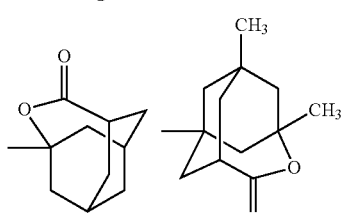

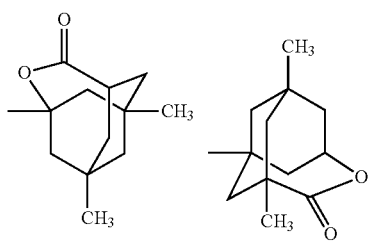

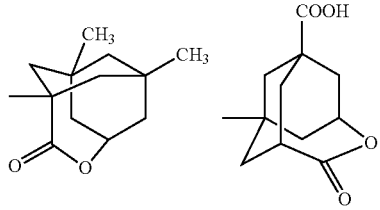

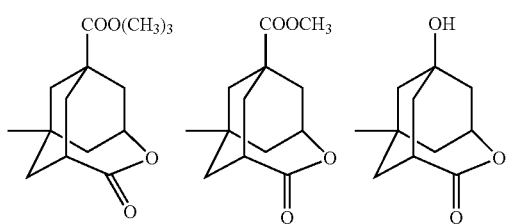

-continued

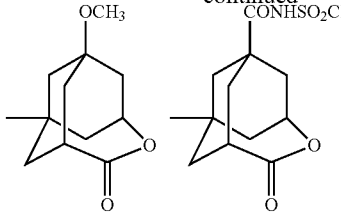

[Chem. 17]

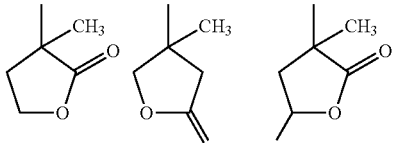

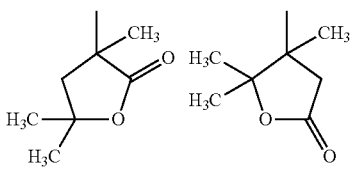

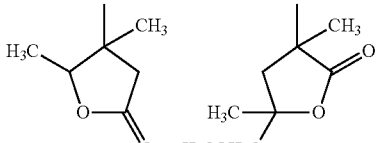

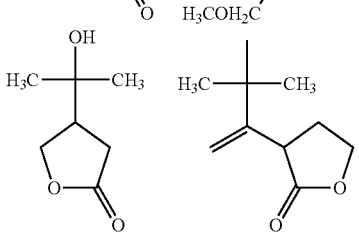

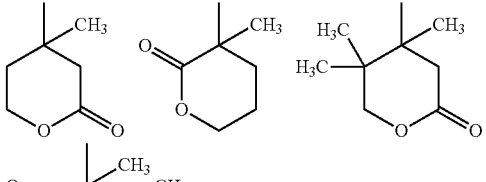

In the above formulas, methyl ($CH_3$) groups may independently be replaced with ethyl groups.

In the case of using high energy radiation of 300 nm or less wavelength e.g. ArF excimer laser radiation as exposure light, the acid labile group is preferably a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an acid labile group containing an alicyclic hydrocarbon structure such as adamantyl or isobornyl, or a lactone-containing acid labile group.

The neutral hydroxyl-containing group (iii) as $R^3$ is a monovalent organic group in which one or two or more hydrogen atoms on any carbon atom of the after-mentioned organic group (iv) is substituted with a hydroxyl group.

It is preferable that the hydroxyl group is approximately neutral. The neutral hydroxyl group, when introduced into the resist resin, does not participate in the function of increasing the solubility of the resin in the alkali solution but undergoes reaction with the after-mentioned cross-linking agent to form a cross-link such as ester bond, ureido bond etc. so that the resin, which has been soluble in the aqueous alkali solution, can be made insoluble or difficult to solve in the aqueous alkali solution.

The monovalent organic group is represented by the general formula (4):

$$—W^2—(OH)_p \tag{4}$$

where $W^2$ represents an alicyclic hydrocarbon group, or an aliphatic hydrocarbon group of valency p+1 or an organic unit formed by combination thereof; and p represents an integer of 1 to 3.

The alicyclic hydrocarbon group as $W^2$ can be either monocyclic or polycyclic. It is preferable that the alicyclic hydrocarbon group is polycyclic and saturated. Further, the alicyclic hydrocarbon group is preferably of 5 to 15 carbon atoms.

The aliphatic hydrocarbon group is a group in which p+1 hydrogen atoms are eliminated from a branched or unbranched saturated hydrocarbon. It is preferable that p is 1. The aliphatic hydrocarbon group is preferably of 1 to 10 carbon atoms, more preferably 1 to 8 carbon atoms. Particularly preferred are ethylene and methylene.

There can also be used $C_1$-$C_4$ halogenated alkylene groups, each of which is obtained by substitution of a part or all of hydrogen atom of the aliphatic hydrocarbon group (preferably ethylene group or methylene group) with a halogen atom, preferably a fluorine atom.

Depending on the purpose of control of the properties of the fluorine-containing polymer compound for use in the resist composition, $R^3$ can be selected as appropriate from the above range. In order to attain a wide exposure margin during the formation of a line pattern by underexposure, the monovalent organic group of the general formula (4) is preferably a group of the following general formula (8):

[Chem. 18]

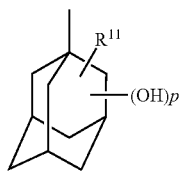

(8)

where $R^{11}$ represents a hydrogen atom, an alkyl group or a $C_1$-$C_5$ alkoxyl group; and p represents an integer of 1 to 3.

The alkyl group as $R^{11}$ is preferably of 1 to 5 carbon atoms. Examples of the alkyl group as $R^{11}$ are methyl, ethyl, propyl, isopropyl, n-butyl, isobutyl, tert-butyl, pentyl, isopentyl and neopentyl. Among others, a lower alkyl group is preferred. Particularly preferred is methyl.

The alkoxyl group as $R^{11}$ is a straight or branched group in which an oxygen atom is bonded to the above alkyl group and is preferably of 1 to 5 carbon atoms, more preferably 1 to 3 carbon atoms. Further, p is an integer of 1 to 3, preferably 1. There is no particular limitation of the bonding position of the hydroxyl group. It is preferable that the hydroxyl group is bonded in 3-position of the adamantyl moiety.

There can be exemplified alicyclic group-containing monovalent organic groups as follows as preferred examples of $R^3$ other than the monovalent organic group of the general formula (8). The monovalent organic group $R^3$ is not however limited to these examples.

[Chem. 19]

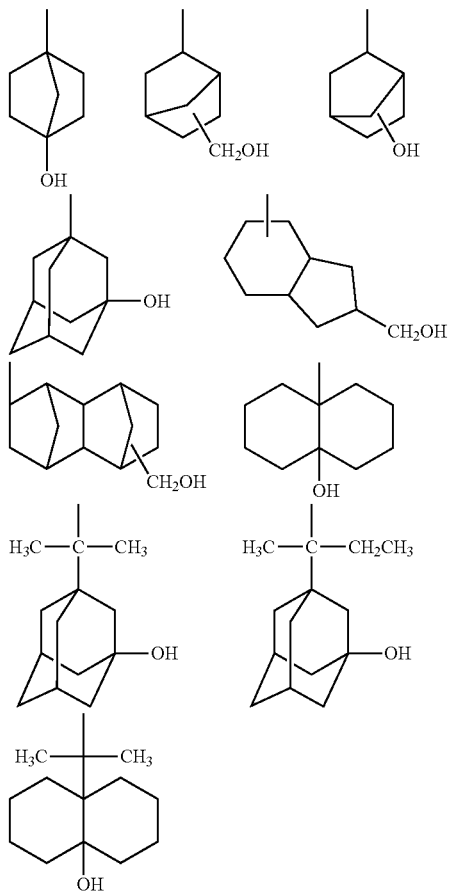

As $R^3$, there can also be used alcoholic hydroxyl containing groups such as hydroxymethyl, 2-hydroxyethyl, 3-hydroxypropyl, 4-hydroxybutyl, 5-hydroxypentyl and 2,2-dimethyl-3-hydroxypropyl.

There is no particular limitation on the organic group (iv) as $R^3$ as long as the organic group (iv) does not contain an acid labile group or a neutral hydroxyl group. As such an organic group, any monovalent organic group selected from a $C_1$-$C_{20}$ straight, branched or cyclic alkyl group and an aryl group is usable. The alkyl and aryl groups may each have a substituent such as a $C_1$-$C_{20}$ straight, branched or cyclic alkyl or aryl group. Herein, a tertiary alkyl group is not applicable as the organic group in view of the fact that the tertiary alkyl group generally serves as an acid labile group. An arbitrary number of hydrogen atoms bonded to any carbon atom of $R^3$ may be substituted with a fluorine atom.

The alkyl group is a $C_1$-$C_{20}$ straight, branched or cyclic alkyl group as mentioned above and is preferably of 1 to 12 carbon atoms. Examples of the alkyl group are methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-docecyl. Among others, lower alkyl groups are preferred. Particularly preferred are methyl, ethyl, n-propyl and i-propyl. Examples of the fluorine-substituted alkyl group are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl.

As the substituent of the straight or branched alkyl group, there can be used a cyclic alkyl group as mentioned below, such as cyclohexyl or adamantyl, without particular limitation. This cyclic alkyl substituent may further be substituted as in the case of the following examples.

The cyclic alkyl group is preferably of 3 to 12 ring carbons, more preferably 3 to 7 ring carbons. Preferred example of the cyclic alkyl group are: monocyclic alkyl groups such as cyclopropyl, cyclobutyl, cyclopentyl, cyclohexyl, cycloheptyl, cyclooctyl, cyclodecanyl, cyclododecanyl and 4-tert-butylcyclohexyl; and polycyclic alkyl groups such as those of 7 to 15 ring carbons e.g. adamantyl, noradamantyl, decalin residue, tricyclodecanyl, tetracyclododecanyl, norbornyl and cedrol. Among others, particularly preferred are adamantyl, decalin residue, norbornyl, cedrol, cyclohexyl, cycloheptyl, cyclooctyl, cyclodecanyl, cyclododecanyl and tricyclodecanyl. The cyclic alkyl groups may be bonded together to form a spiro ring, preferably a $C_3$-$C_6$ spiro ring. One or two or more hydrogen atoms on the ring carbons of the above organic group may be each independently substituted with a substituent such as a $C_1$-$C_{20}$ alkyl or substituted alkyl group. One or two or more hydrogen atoms on the carbon-hydrogen bond may further be substituted with fluorine or trifluoromethyl.

The $C_1$-$C_{20}$ straight, branched or cyclic alkyl group as the substituent is preferably a lower alkyl group, more preferably an alkyl group selected from the group consisting of methyl, ethyl, propyl and isopropyl. This alkyl group may be substituted with a halogen atom, notably a fluorine atom.

[Production Method of Fluorine-Containing Carboxylic Acid Amide]

There is no particular limitation on the production method of the fluorine-containing unsaturated carboxylic acid amide of the general formula (1) in the present invention. For example, the fluorine-containing unsaturated carboxylic acid amide of the general formula (1) can be produced by the following procedures. A fluorine-containing unsaturated carboxylic acid halide is first prepared according the reaction schemes [1] to [4].

Reaction scheme [1]

[Chem. 20]

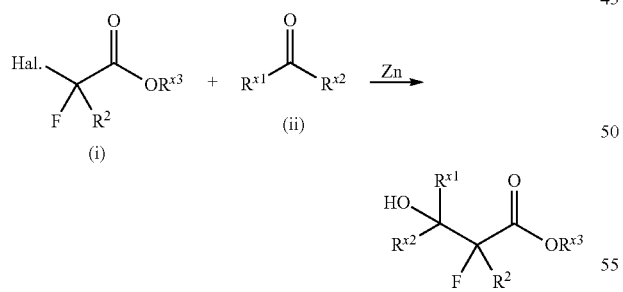

Reaction scheme [2]

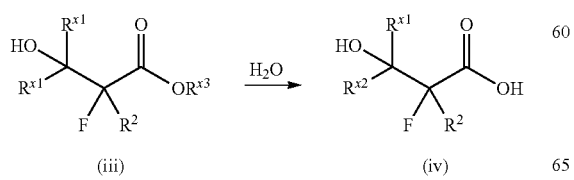

Reaction scheme [3]

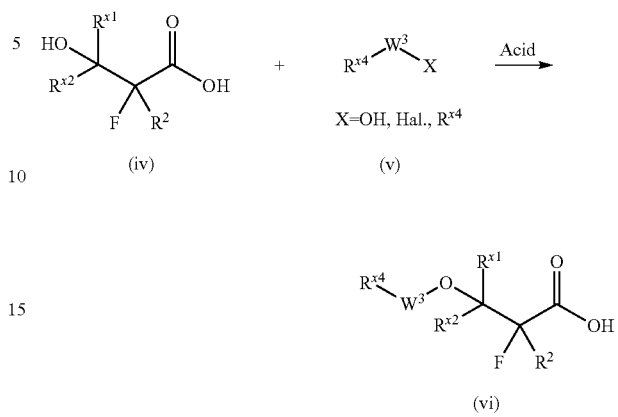

Reaction scheme [4]

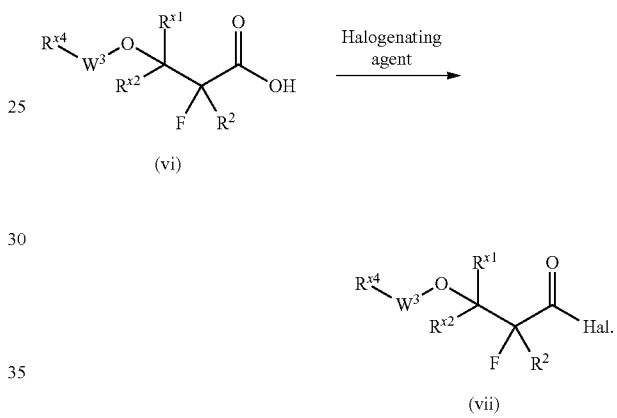

A fluorine-containing unsaturated carboxylic acid amide is produced by reaction of the fluorine-containing unsaturated carboxylic acid halide with ammonia (ammonium) according the reaction scheme [5-1].

Reaction scheme [5-1]

[Chem. 21]

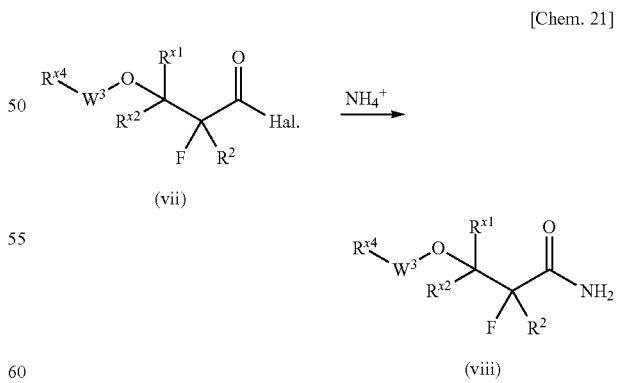

Similarly, a fluorine-containing unsaturated carboxylic acid amide having a hydroxyl group is produced by reaction of the fluorine-containing unsaturated carboxylic acid halide with a hydroxyl-containing amine according to the reaction scheme [5-2].

Reaction scheme [5-2]

[Chem. 22]

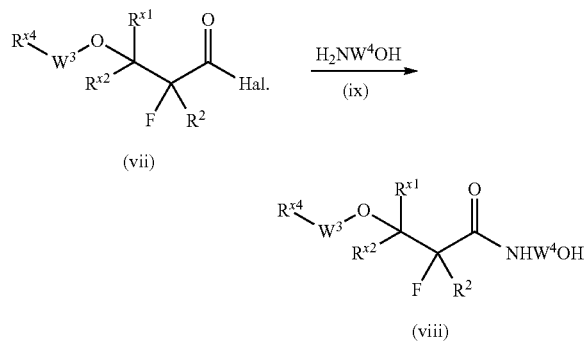

A fluorine-containing unsaturated carboxylic acid amide compound is produced by reaction of the fluorine-containing unsaturated carboxylic acid halide with an amine according to the reaction scheme [5-3].

Reaction scheme [5-3]

[Chem. 23]

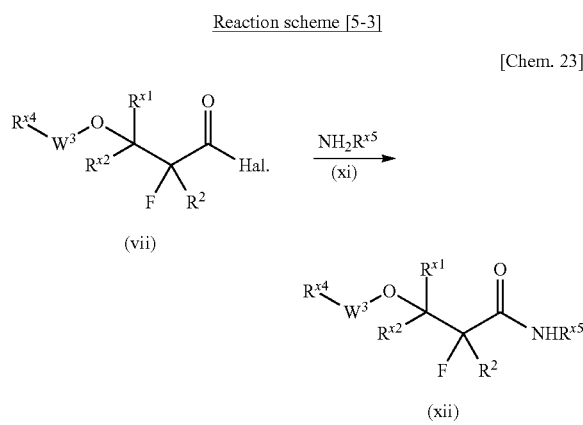

A fluorine-containing unsaturated carboxylic acid secondary amide is produced by reaction of the fluorine-containing unsaturated carboxylic acid amide with an organic halide according to the reaction scheme [6].

Reaction scheme [6]

[Chem. 24]

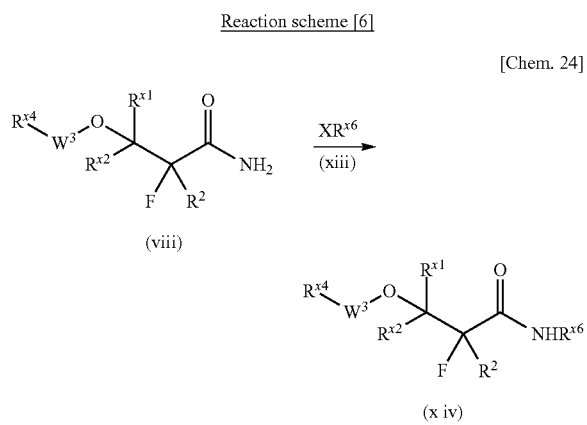

A fluorine-containing unsaturated carboxylic acid tertiary amine is produced by reaction of the fluorine-containing unsaturated carboxylic acid secondary amine with an organic halide according to the reaction scheme [7].

Reaction scheme [7]

[Chem. 25]

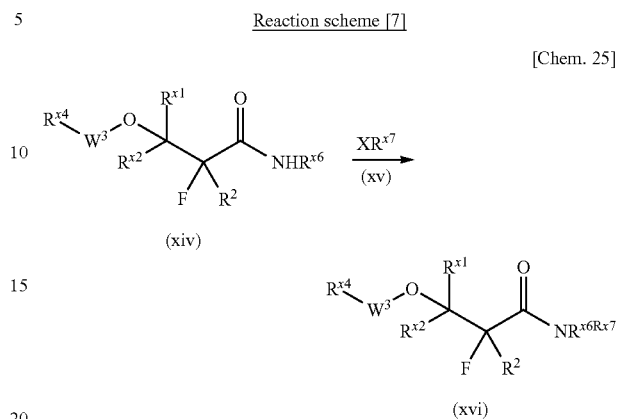

In the reaction schemes [1] to [7], $R^{X4}$—$W^3$—O— and $R^2$ are the same as $R^0$ and $R^2$ defined in the general formula (1), respectively; $R^{X1}$, $R^{X2}$ and $R^{X3}$ each independently represent a monovalent organic group; and $R^{X1}$ may alternatively represents a hydrogen atom. Herein, $R^{X1}$ and $R^{X2}$ correspond to $R^4$ and $R^5$ in the case where, in the general formula (1), $W^1$ is substituted methylene represented by the general formula (3). The definitions of $R^4$ and $R^5$ can be thus applied to $R^{X1}$ and $R^{X2}$, respectively. Each of $R^{X1}$ and $R^{X2}$ is preferably a lower alkyl group. Specific examples of $R^{X1}$, $R^{X2}$ are methyl, ethyl, propyl, butyl, cyclopentyl, cyclohexyl, norbornyl, adamantyl and fluorine-substituted groups thereof such as trifluoromethyl, 2,2,2-trifluoroethyl, 1-(trifluoromethyl)ethyl and 3,3,3-trifluoropropyl. $R^{X1}$ and $R^{X2}$ may be bonded to each other to form a cyclic group such as cyclopentyl, cyclohexyl or cycloheptyl. Further, $R^{X3}$ represents an ester protecting group; $R^{X5}$, $R^{X6}$ and $R^{X7}$ correspond to specific forms of $R^3$ in the general formula (1); $W^3$ and $W^4$ each represent a linking group; and $W^3$—O—$CR^{X1}R^{X2}$ corresponds to specific forms of $W^1$ in the general formula (1).

Each of the reaction steps will be next explained in detail below.

Reaction Scheme [1]: a halogen-containing carboxylic acid ester (i), which has at least one fluorine atom and one halogen atom (other than fluorine atom) at α-position, reacts with a carbonyl compound (ii) in the presence of zinc under anhydrous conditions, to thereby form a hydroxycarboxylic acid ester (iii). (This reaction is known as Reformatsky reaction.)

Reaction Scheme [2]: the hydroxycarboxylic acid ester (iii) obtained in the reaction scheme [1] undergoes hydrolysis to form a hydroxycarboxylic acid (iv).

Reaction Scheme [3]: the hydroxycarboxylic acid (iv) obtained in the reaction scheme [2] reacts with a carboxylic acid having a polymerizable double bond or an anhydride or halide thereof [v] to thereby form an unsaturated carboxylic acid (iv).

Reaction Scheme [4]: the unsaturated carboxylic acid (iv) obtained in the reaction scheme [3] undergoes hydrogenation with the use of a halogenating agent such as thionyl chloride to thereby faun an unsatureated carboxylic acid halide (vii).

Reaction Scheme [5-1]: the unsatureated carboxylic acid halide (vii) obtained in the reaction scheme [4] reacts with an ammonia water or an ammonium salt to form an unsaturated carboxylic acid amide (viii).

Reaction Scheme [5-2]: the unsatureated carboxylic acid halide (vii) obtained in the reaction scheme [4] reacts with a hydroxylamine (ix) to form a fluorine-containing unsaturated N-(hydroxyalkyl) substituted carboxylic acid amide (x).

Reaction Scheme [5-3]: the unsaturated carboxylic acid halide (vii) obtained in the reaction scheme [4] reacts with a primary amine to form a fluorine-containing unsaturated N-substituted carboxylic acid amide (x).

Reaction Scheme [6]: the unsaturated carboxylic acid amide (viii) obtained in the reaction scheme [5-1] reacts with a halide (xiii) to form a fluorine-containing unsaturated N-substituted carboxylic acid amide (xiv).

Reaction Scheme [7]: the unsaturated carboxylic acid amide (viii) obtained in the reaction scheme [5-1] reacts with a halide (xv) to form a fluorine-containing unsaturated N,N-disubstituted carboxylic acid amide (xvi).

There is no particular limitation on the organic solvent usable in the reaction scheme [1] or [3] as long as the organic solvent is not involved in the reaction under the respective reaction conditions. Examples of the organic solvent usable in the reaction are: aliphatic hydrocarbons such as pentane, hexane and heptanes; aromatic hydrocarbons such as benzene, toluene and xylene; nitriles such as acetonitrile, propionitrile, phenylacetonitrile, isobutylonitrile and benzonitrile; acid amides such as dimethylformamide, dimethylacetoamide, methylformamide, formamide and hexamethyl phosphoramide; and lower ethers such as tetrahydrofuran, 1,2-dimethoxyethane, 1,4-dioxane, diethyl ether, 1,2-epoxyethene, dibutyl ether, thert-butyl methyl ether and substituted tetrahydrofurane. Among others, tetrahydrofuran and dimethylformaldehyde are preferred. These organic solvents can be used solely or in combination of two or more thereof. The organic solvent used is not limited to the above. The amount of the organic solvent used is generally about 1 to 100 parts by weight, preferably 1 to 10 parts by weight, per 1 part by weight of the starting material. It is preferable in the reaction scheme [1] to remove a moisture content as much as possible from the organic solvent. The moisture content of the organic solvent is more preferably 50 ppm or less.

In the reaction scheme [3], it is preferable to remove a moisture content as much as possible from the organic solvent. However, the moisture content is not necessarily completely removed from the organic solvent. There would be no problem when the organic solvent has as much a moisture content as ordinarily contained in an industrially available organic solvent. The industrially available organic solvent can be thus used as it is.

It is further preferable in the reaction scheme [1] that the zinc metal has been activated by any known technique before use. For preparation of such activated zinc metal, there can be used: a process in which the activated zinc metal is obtained by reduction of a zinc salt e.g. zinc chloride with potassium, magnesium, lithium etc.; a process in which the zinc metal is activated by treatment with hydrochloric acid; a process in which the zinc metal is activated by treating the zinc metal with a copper salt or silver salt in acetic acid and thereby alloying the zinc metal with copper or silver; a process in which the zinc metal is activated by treatment with ultrasonic wave; a process in which the zinc metal is activated by stirring the zinc metal with chlorotrimethylsilane in an ether; a process in which the zinc metal is activated by contact with a copper compound and chlorotrimethylsilane in an aprotic organic solvent; and the like.

The zinc metal can be in any form such as powder foam, particle form, massive form, porous form, abatement form or linear form. The reaction temperature is generally about −78 to 120° C. The reaction time varies depending on the reactant. It is generally convenient to perform the reaction for 10 minutes to 20 hours. The reaction pressure is generally at or around atmospheric pressure. The other reaction conditions can be set as in the case of similar reactions using zinc metal known to those skilled in the art.

In the reaction scheme [2], the hydrolysis reaction is performed in the presence of a base and water. Examples of the base usable in the reaction are: organic bases such as trimethylamine, triethylamine, diisopropylethylamine, tri-n-propylamine, tri-n-butylamine, dimethyllaurylamine, dimethylaminopyridine, N,N-dimethylaniline, dimethylbenzylamine, 1,8-diazabicyclo[5.4.0]undec-7-ene, 1,4-diazabicyclo[2.2.2]octane, pyridine, 2,4,6-trimethylpyridine, pyrimidine, pyridazine, 3,5-lutidine, 2,6-lutidine, 2,4-lutidine, 2,5-lutidine and 3,4-lutidine; and inorganic bases such as sodium hydroxide, potassium hydroxide, sodium carbonate and calcium hydroxide.

It suffices to use the base in an amount of 1 mol or more, per 1 mol of the reaction substrate, in the reaction scheme [2]. The amount of the base used is generally preferably 1 to 10 mol, more preferably 1 to 5 mol, per 1 mol of the reaction substrate.

In the reaction schemes [2] to [7], the reaction temperature depends on the reagent used. The reaction temperature is generally about −78 to 120° C. The reaction time also depends on the reagent used. It is generally convenient to perform the reaction at about 10 minutes to 20 hours. The reaction pressure is generally at or around atmospheric pressure. The other reaction conditions can be set as in the case of similar reactions known to those skilled in the art.

In the reaction scheme [3], the amount of the polymerizable double bond-containing carboxylic acid, carboxylic acid anhydride or carboxylic acid halide used is generally 0.8 to 5 mol, preferably 1 to 3 mol, more preferably 1 to 2 mol, per 1 mol of the reaction substrate.

Further, an acid may be used as a catalyst in the reaction scheme [3]. Examples of the acid usable as the catalyst are hydrochloric acid, methanesulfonic acid, trifluoromethanesulfonic acid and trifluoroacetic acid. Among others, methanesulfonic acid and trifluoromethnesulfonic acid are preferred.

It suffices to use the acid in an amount of 1 mol or less per 1 mol of the reaction substrate in the reaction scheme [3]. The amount of the acid used is generally preferably 0.1 to 1 mol, more preferably 0.1 to 0.5 mol, per 1 mol of the reaction substrate.

There can be used, as the halogenating agent in the reaction scheme [4], one kind, or a mixture of two or more kinds, selected from thionyl halides, oxalyl halogenides, phosphorus trihalides, phosphrous pentahalides, phosphorous oxyhalides, carbonyl halides and trihalomethyl haloformates. In the case where halogen is chlorine, the chlorinating agent can be selected from thionyl chloride, sulfuryl chloride, phosphorous trichloride, phosphrous pentachloride, phosphoric trichloride acid and oxalyl chloride. Among others, thionyl chloride and phosphorus trichloride acid are particularly preferred.

It suffices to use the halogenating agent in an amount of 1 mol or more per 1 mole of the reaction substrate in the reaction scheme [4]. The amount of the halogenating agent used is generally preferably 1 to 10 mol, more preferably 1 to 5 mol, per 1 mole of the reaction substrate.

In the reaction scheme [5-1], the ammonium ($NH^{4+}$) can be used in the form of ammonia, ammonium carbonate, ammonium chloride, ammonium sulfate, ammonium nitrate, ammonium acetate, ammonium phosphate etc. Among others, preferred are ammonia and ammonium carbonate.

It suffices to use the ammonium ($NH_4^+$) in an amount of 1 mol or more per 1 mol of the reaction substrate in the reaction scheme [5-1]. The amount of the ammonium used is generally preferably 1 to 10 mol, more preferably 1 to 5 mol, per 1 mol of the reaction substrate.

In the reaction scheme [5-2], the definition of $W^4$ in the hydroxyamine ($H_2NW^4OH$) of the general formula (ix) is the same as that of $W^2$ as defined above.

It suffices to use the hydroxyamine in an amount of 1 mol or more per 1 mol of the reaction substrate in the reaction scheme [5-2]. The amount of the hydroxyamine used is generally preferably 1 to 10 mol, more preferably 1 to 5 mol, per 1 mol of the reaction substrate.

In the reaction scheme [5-3], the definition of $R^{X5}$ in the amine ($NH_2R^{X5}$) of the general formula (xi) is the same as defined above.

It suffices to use the amine in an amount of 1 mol or more per 1 mol of the reaction substrate in the reaction scheme [5-3]. The amount of the amine used is generally preferably 1 to 10 mol, preferably 1 to 5 mol, per 1 mol of the reaction substrate.

In the reaction schemes [6] and [7], the definitions of $R^{X5}$ and $R^{X6}$ in the halides ($XR^{X5}$, $XR^{X6}$) of the general formula (xiii) and (xv) are the same as defined above.

It suffices, in the reaction scheme [6] or [7], to use the halide in an amount of 1 mol or more, per 1 mol of the reaction substrate. The amount of the halide used is generally preferably 1 to 10 mol, more preferably 1 to 5 mol, per 1 mol of the reaction substrate.

The following are examples of the amine of the general formula (ix) or (xi) used in the reaction scheme [5-2] or [5-3]. In the present specification, carbon atoms and hydrogen atoms are not indicated in each structural formula according to conventional practice.

[Chem. 26]

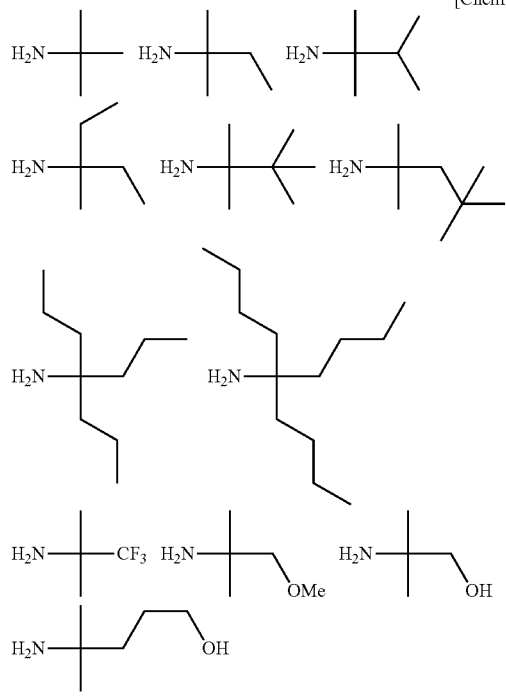

[Chem. 27]

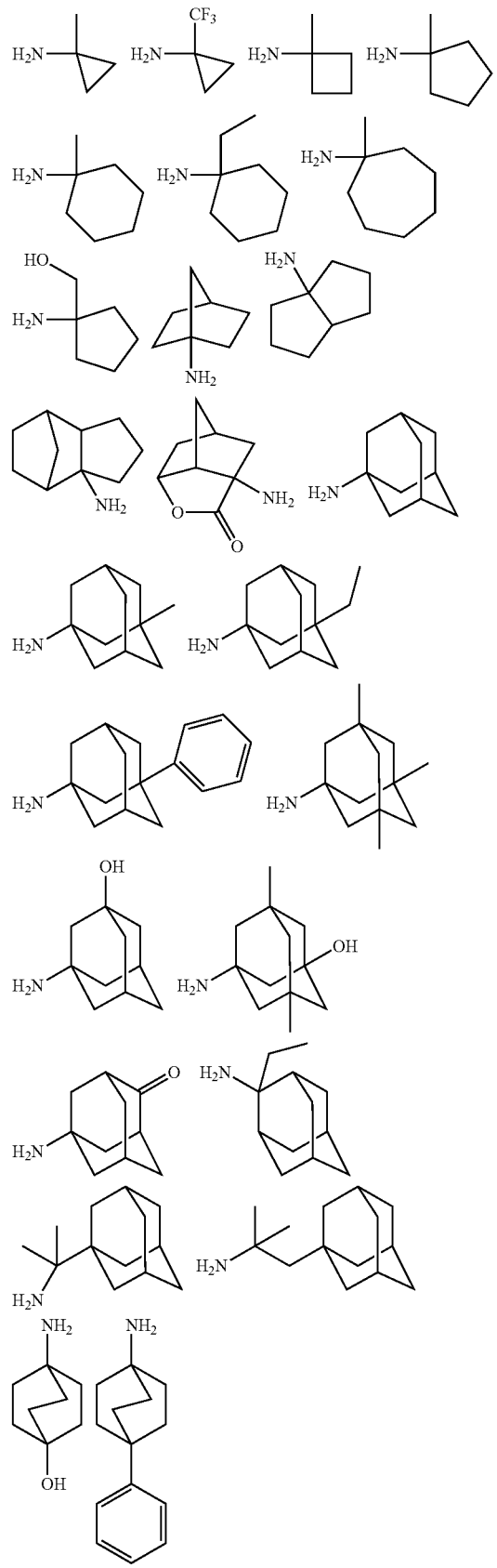

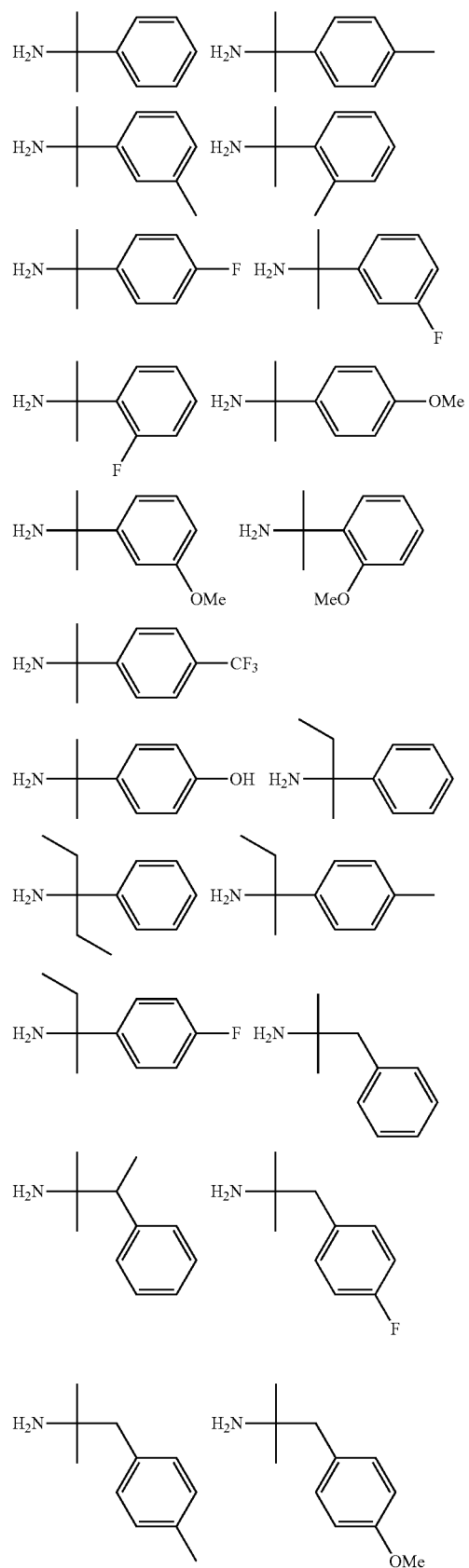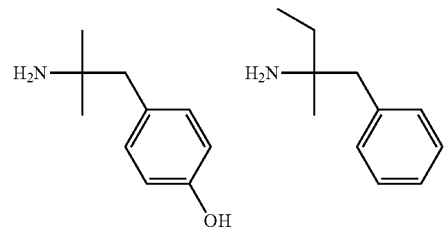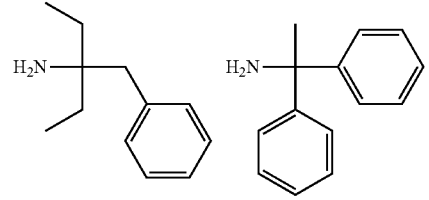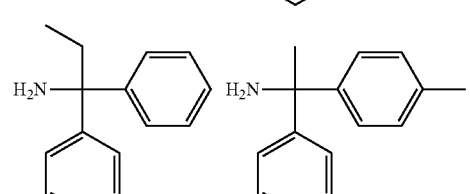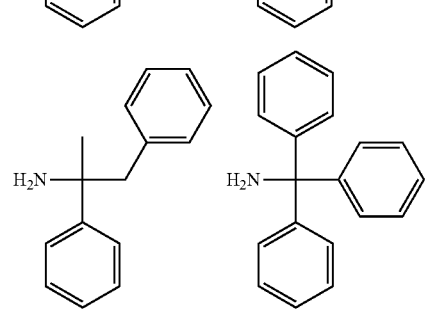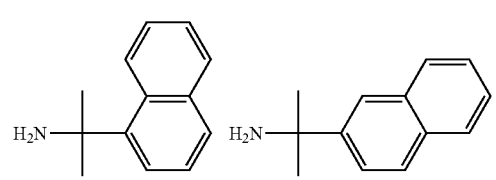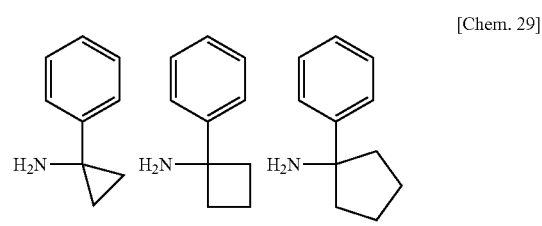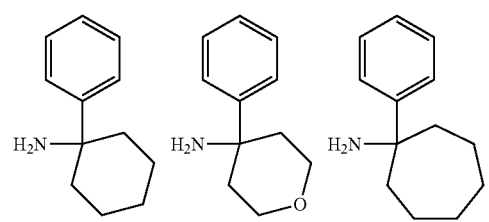

-continued

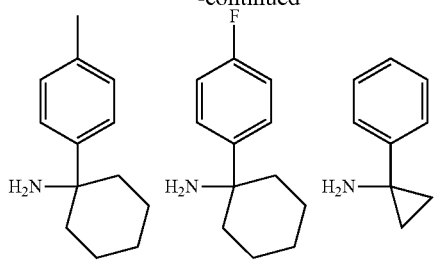

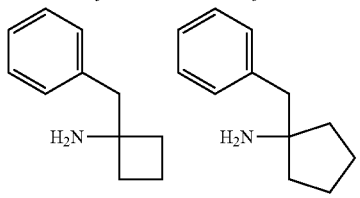

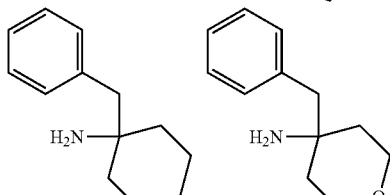

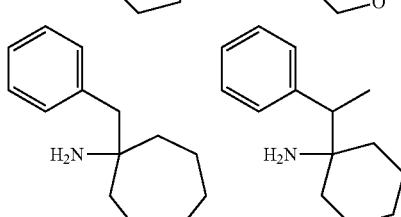

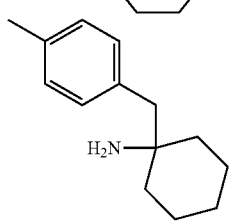

[Chem. 30]

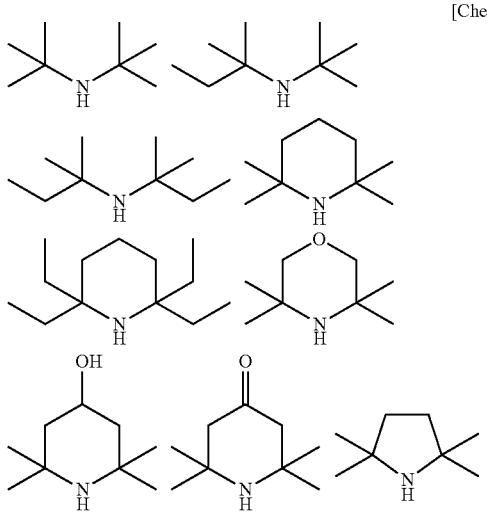

-continued

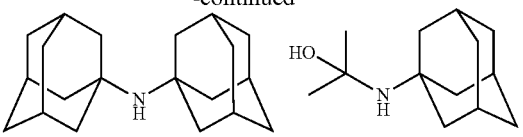

Further, purification operation such as washing, solvent separation and drying may be performed between the reaction steps of the reaction schemes [1] to [7].

[Fluorine-Containing Polymer Compound]

The fluorine-containing polymer compound having the repeating unit (a) of the general formula (2) is formed by cleavage of the double bond of the unsaturated double bond-containing group ($R^0$) of the fluorine-containing unsaturated carboxylic acid amide of the general formula (1).

[Chem. 31]

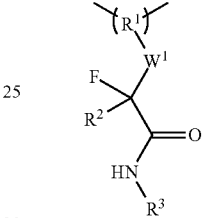

(2)

This polymerization reaction does not cause changes in any bonds and structural moieties of the monomer unit other than the polymerizable double bond.

In the fluorine-containing polymer compound, the repeating unit (a) can be included solely or in combination of any other repeating unit. The other repeating unit is selected as appropriate to control the properties of the resist material, such as dry etching resistance, suitability for alkali developer (standard developer), adhesion to substrate, resist profile and commonly required resist performance e.g. resolution, heat resistance, sensitivity etc.

As $R^3$ is either a hydrogen atom, an acid labile group, a neutral hydroxyl-containing group or any other group in the fluorine-containing carboxylic acid amide of the general formula (1) as mentioned above, the repeating unit (a) of the general formula (2) is herein specifically referred to as a repeating unit (a-1) when $R^3$ is a hydrogen atom, a repeating unit (a-2) when $R^3$ is an acid labile group, a repeating unit (a-3) when $R^3$ is a neutral hydroxyl-containing group, and a repeating unit (a-4) when $R^3$ is any other group.

The constitutional ratio of the repeating unit (a-1) and the other repeating unit in the fluorine-containing polymer compound (occasionally called "base resin" in the present specification) is set in such a manner that the amount of the repeating unit (a-1) in the base resin is 0.1 to 70 mol %, preferably 1 to 60 mol %, more preferably 5 to 40 mol %. If the amount of the repeating unit (a-1) is less than 0.1 mol %, the base resin cannot attain sufficient solubility in an alkali developer in an unexposed state or after exposure. In addition, the resulting resist composition cannot form a pattern with high precision due to the occurrence of swelling or pattern collapse. If the amount of the repeating unit (a-1) exceeds 70 mol %, the solubility changing function of the base resin of the positive or negative resist composition becomes deteriorated so that the resulting resist composition cannot form a pattern with good rectangular profile. It is thus unfavorable that the amount of the repeating unit (a-1) is less than 0.1 mol % or exceeds 70 mol %.

The repeating unit other than the repeating unit (a-1) includes at least either of a positive resist monomer unit having an acid labile group or a negative resist monomer unit having a cross-linking site and may includes the after-mentioned repeating unit (b). The amount of either the positive resist monomer unit having the acid labile group or the negative resist monomer unit having the cross-linking site in the repeating unit other than the repeating unit (a-1) is generally 10 to 100 mol %, preferably 15 to 80 mol %, more preferably 20 to 70 mol %. If the amount of the positive or negative resist monomer unit is less than 10 mol %, the base resin cannot attain sufficient solubility or cross-linking. The resulting resist compound thus cannot achieve basic resist performance. It is thus unfavorable that the amount of the positive or negative resist monomer unit is less than 10 mol %. The repeating unit (b) is the balance of the repeating unit other than the repeating unit (a-1), i.e., is not necessarily contained but is preferably contained in an appropriate amount for improvements in adhesion and etching resistance.

The constitutional ratio of the repeating unit (a-2) and the other repeating unit(s) in the fluorine-containing polymer compound is set in such a manner that the amount of the repeating unit (a-2) in the base resin is 0.1 to 70 mol %, preferably 1 to 60 mol %, more preferably 5 to 40 mol %. If the amount of the repeating unit (a-2) is less than 0.1 mol %, the base resin cannot attain sufficient solubility in an alkali developer or after exposure. In addition, the resulting resist composition cannot form a pattern with high precision. If the amount of the repeating unit (a-1) exceeds 70 mol %, it is difficult to maintain the performance required of the resist resin, such substrate adhesion and etching resistance, so that the resulting resist composition cannot form a pattern with good rectangular profile. It is thus unfavorable that the amount of the repeating unit (a-2) is less than 0.1 mol % or exceeds 70 mol %.

As the repeating unit(s) other than the repeating unit (a-2), any of the repeating unit (a-1), the repeating unit (a-4) and the after-mentioned repeating unit (b) can be contained. The repeating unit (a-1) may be used in place of a part or all of monomer unit having a solubility developing group such as a hydroxyl or carboxyl group among the repeating unit (b).

The constitutional ratio of the repeating unit (a-3) and the other repeating unit(s) in the fluorine-containing polymer compound is set in such a manner that the amount of the repeating unit (a-3) in the base resin is 0.1 to 70 mol %, preferably 1 to 60 mol %, more preferably 5 to 40 mol %. If the amount of the repeating unit (a-3) is less than 0.1 mol %, the base resin cannot attain sufficient solubility in an alkali developer in an unexposed state. Further, the base resin, when used in the negative resist composition, cannot be cured properly due to insufficient cross-linking by exposure so that the resist composition cannot form a pattern with high precision due to the occurrence of swelling or pattern collapse. If the amount of the repeating unit (a-1) exceeds 70 mol %, it is difficult to maintain the performance required of the resist resin, such substrate adhesion and etching resistance, so that the resulting resist composition cannot form a pattern with good rectangular profile. It is thus unfavorable that the amount of the repeating unit (a-3) is less than 0.1 mol % or exceeds 70 mol %.

As the repeating unit(s) other than the repeating unit (a-3), any of the repeating unit (a-1), the repeating unit (a-4) and the after-mentioned repeating unit (b) can be contained. The repeating unit (a-1) may be used in place of a part or all of monomer unit having a solubility developing group such as a hydroxyl or carboxyl group among the repeating unit (b).

In the fluorine-containing polymer compound of the present invention, the repeating unit (a-4) does not serve as a positive or negative resist monomer unit but imparts solubility. The amount of the repeating unit (a-4) in the sum of all of the repeating units of the base resin is generally 0.1 to 70 mol %, preferably 1 to 60 mol %, more preferably 5 to 40 mol %. The base resin is not limited to those having the positive resist monomer unit with the acid labile group or the negative resist monomer unit with the cross-linking site. As the base resin, there can suitably be used those in which the repeating unit (a-4) coexists with the repeating unit (a-2) or the repeating unit (a-3). If the amount of the repeating unit (a-4) is less than 0.1 mol %, the repeating unit (4) does not impart sufficient solubility to the base resin so that there is no point in the addition of the repeating unit (4). If the amount of the repeating unit (a-4) exceeds 70 mol %, the base resin cannot attain sufficient positive or negative resist resin function. It is thus unfavorable that the amount of the repeating unit (a-4) is less than 0.1 mol % or exceeds 70 mol %.

The fluorine-containing polymer compound of the present invention has a weight-average molecular weight of 1000 to 1000000, more preferably 2000 to 500000, as measured by gel permeation chromatography (GPC). If the weight-average molecular weight of the fluorine-containing polymer compound is less than 1000, a film of the resulting resist composition cannot be formed with sufficient strength. If the weight-average molecular weight of the fluorine-containing polymer compound exceeds 1000000, the solubility of the polymer compound in the solvent becomes deteriorated so that it is unfavorably difficult to apply a smooth film of the resist composition. The molecular weight distribution (Mw/Mn) of the fluorine-containing polymer compound is preferably in the range of 1.01 to 5.00, more preferably 1.01 to 4.00, still more preferably 1.01 to 3.00, most preferably 1.10 to 2.50.

[Repeating Unit (b)]

The fluorine-containing polymer compound may contain, in addition to the repeating unit (a), any selected from various kinds of monomer units to control the properties of the resist material, such as dry etching resistance, suitability for standard developer, adhesion to substrate, resist profile and commonly required resist performance e.g. resolution, heat resistance, sensitivity etc. as the repeating unit (b).

As the repeating unit (b), there can be used those derived from the following monomers. The repeating unit (b) is not however limited to these examples. The addition of the repeating unit (b) enables fine control of the properties required of the resin, notably (1) solubility in solvent, (2) film forming property (glass transition temperature), (3) alkali developability, (4) film wear resistance (hydrophilicity/hydrophobicity, selection of alkali-soluble group), (5) adhesion of unexposed resist resin to substrate and (6) dry etching resistance.

It is preferable to use, as the repeating unit (b), a monomer unit derived from a lactone group-containing acrylic or methacrylic acid and a monomer unit derived from a polar group-containing acrylic or methacrylic acid. In this case, the amount of the monomer unit derived from the lactone group-containing acrylic or methacrylic acid is preferably 10 to 60%, more preferably 20 to 50%.

The repeating unit (b) will be explained in more detail below by way of the monomer before the formation of the repeating unit by cleavage of the polymerizable double bond.

As the monomer to form the repeating unit (b), there can be used acrylic esters, fluorine-containing acrylic esters, methacrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylic amides (except for those represented by the general formula (1)), methacrylic amides (except for those represented by the general formula (1)), vinyl esters, allyl esters, olefins, fluorine-containing olefins, norbornene compounds, fluorine-containing norbornene compounds, sulfur dioxide and vinyl silanes. One or more kinds of the above monomer can be used for copolymerization with the monomer of the repeating unit (a) to produce the fluorine-containing polymer compound.

There is no particular limitation on the ester moiety of the acrylic ester or methacrylic ester. Examples of the acrylic ester or methacrylic ester are known acrylic or methacrylic ester compounds: such as acrylic or methacrylic acid alkyl ester e.g. methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, tert-butyl acrylate or methacrylate, amyl acrylate or methacrylate, n-hexyl acrylate or methacrylate, n-octyl acrylate or methacrylate, 2-ethylhexyl acrylate or methacrylate, benzyl acrylate or methacrylate, chlorobenzyl acrylate or methacrylate, octyl acrylate or methacrylate, 2-hydroxyethyl acrylate or methacrylate, 4-hydroxybutyl acrylate or methacrylate, 5-hydroxypentyl acrylate or methacrylate, 2,2-dimethyl-3-hydroxypropyl acrylate or methacrylate, trimethylolpropane monoacrylate or methacrylate, pentaerythritol monoacrylate or methacrylate, furfuryl acrylate or methacrylate, tetrahydrofurfuryl acrylate or methacrylate, lauryl acrylate or methacrylate, 2-hydroxyethyl acrylate or methacrylate, or 2-hydroxypropyl acrylate or methacrylate; acrylate or methacrylate containing an ethylene glycol group, a propylene glycol group or a tetramethylene glycol group; 3-oxocyclohexyl acrylate or methacrylate; adamantyl acrylate or methacrylate; alkyladamantyl acrylate or methacrylate; cyclohexyl acrylate or methacrylate; tricyclodecanyl acrylate or methacrylate; and acrylate or methacrylate having a ring structure such as a norbornene ring. An acrylate compound in which a cyano group is bonded to α-position of the above acrylate, or analog thereof, is also usable.

The fluorine-containing acrylic ester or methacrylic ester is an acrylic ester or methacrylic ester whose ester moiety contains fluorine. A cyano group or trifluoromethyl group may be introduced to α-position of the ester moiety of the fluorine-containing acrylic ester or methacrylic ester. As such an ester monomer containing fluorine in its ester moiety, there can be used an ester in which a part of the ester moiety of the above acrylic ester or methacrylic ester is fluorinated, i.e., an acrylic ester or methacrylic ester having an ester moiety formed with a fluorine-containing alkyl group, or a ring structure in which any of the hydrogen atoms or ring carbons are replaced by a fluorine atom or a fluorine-containing alkyl group e.g. trifluoromethyl, such as a fluorine-containing benzene ring, a fluorine-containing cyclopentane ring, a fluorine-containing cyclohexane ring, a fluorine-containing cycloheptane ring, a fluorine-containing norbornene ring or a fluorine-containing adamantyl ring. Further, tert-butyl ester having a fluorine-containing ester moiety and acrylic ester or methacrylic ester having a cyclohexyl or norbornyl group substituted with a hexafluoroisopropanol group are also usable.

Furthermore, there can preferably be used esters of acrylic acid, methacrylic acid and α,α,α-trifluoroacrylic acid (α-trifluoromethacrylic acid) each containing a lactone group. Any lactone group is usable as long as it has a lactone structure. The lactone group is preferably a 5- to 7-membered lactone group. It is preferable that the 5- to 7-membered lactone ring group is condensed with another ring group to form a bicyclo or spiro structure. The introduction of such a lactone group leads to less line edge roughness and failure in development.

Examples of the lactone group are those indicated by the following formulas (9) and (10).

[Chem. 32]

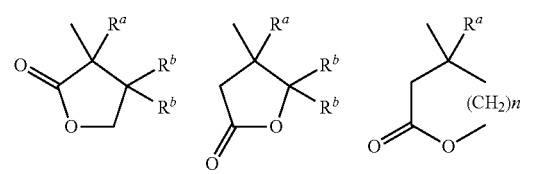

(9)

In the above formulas, $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxyl group, a carboxylic acid group, an alkyloxycarbonyl group or an alkoxy group; and n represents an integer of 1 to 4.

[Chem. 33]

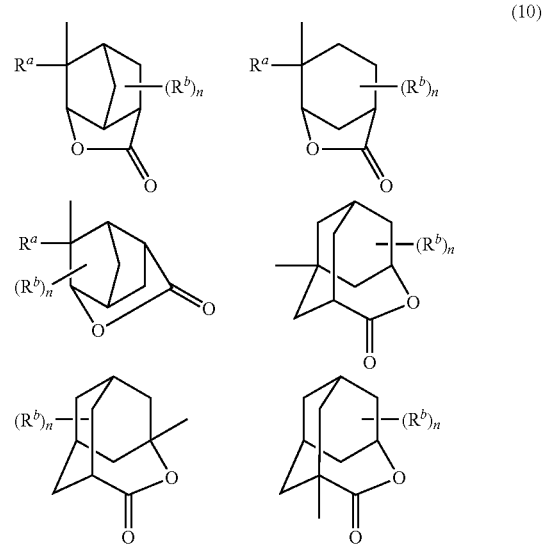

(10)

In the above formulas, $R^b$ each independently represent a hydrogen atom, a $C_1$-$C_4$ alkyl or perfluoroalkyl group, a hydroxyl group, a carboxylic acid group, an alkyloxycarbonyl group or an alkoxy group; and n represents an integer of 1 to 4.

More specifically, the lactone group can be exemplified as follows.

[Chem. 34]

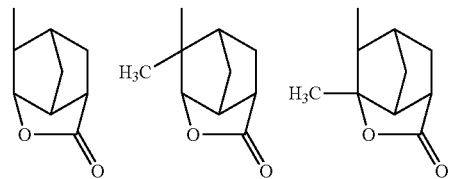

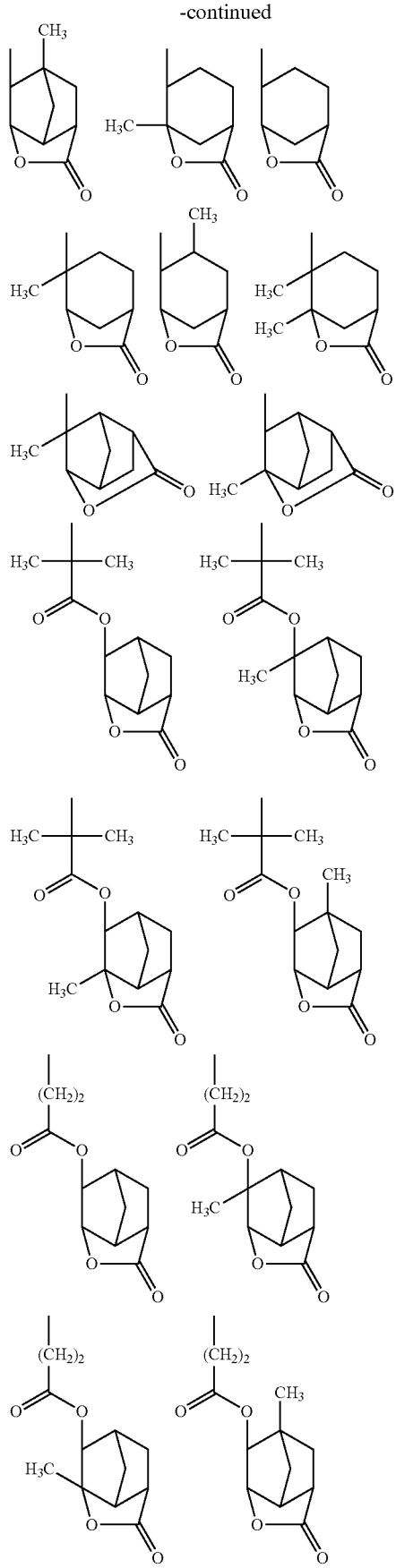
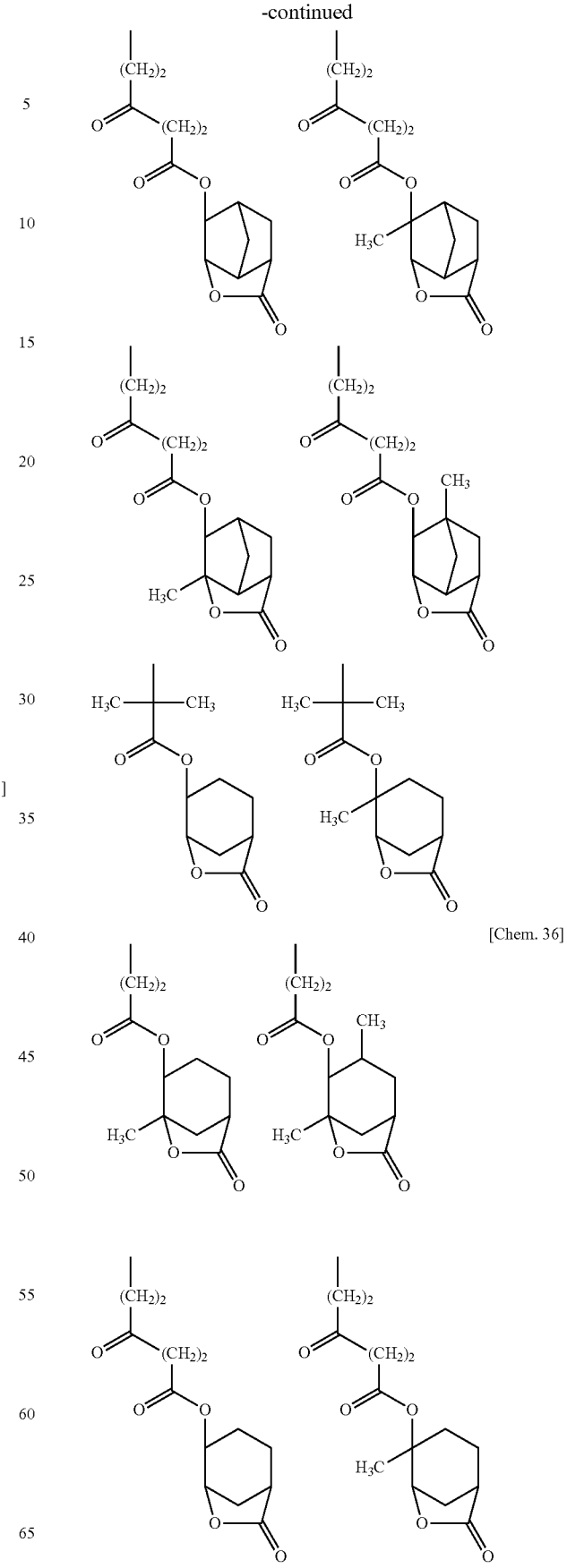
[Chem. 35]
[Chem. 36]

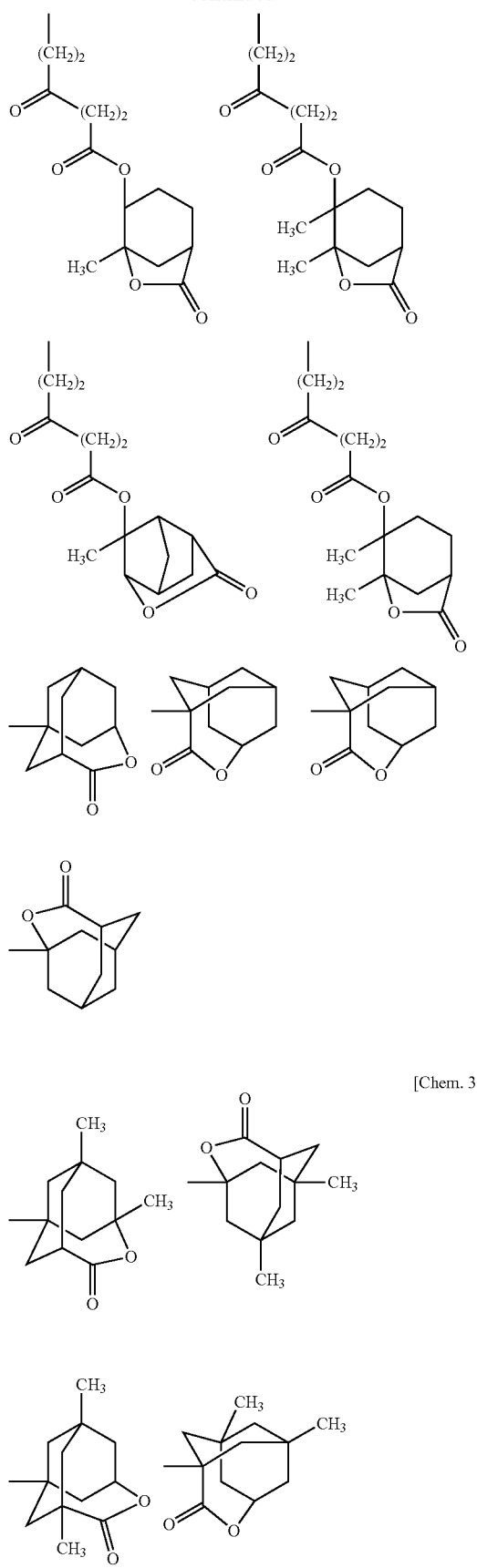
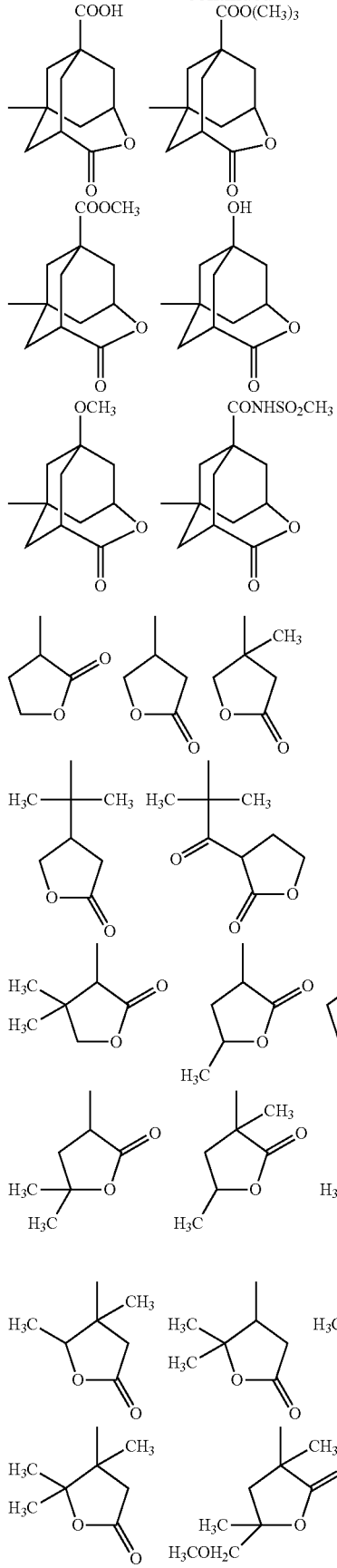
[Chem. 37]
[Chem. 38]
[Chem. 39]

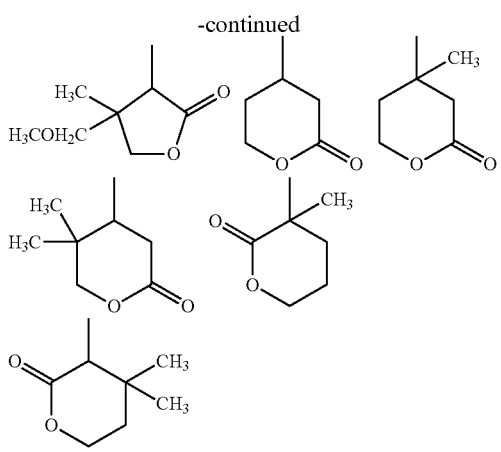

In the above formulas, methyl (CH₃) groups may independently be replaced with ethyl groups.

As the vinyl ether or allyl ether, there can be used those each of which has a $C_1$-$C_{30}$ alkyl group, fluoroalkyl group or alicyclic fluorocarbon group as a substituent and may preferably has a halogen atom (fluorine, chlorine, bromine), a hydroxyl group, an amino group, an aryl group, an alkyl group or an alicyclic hydrocarbon group as another substituent.

Examples of the vinyl ether are: alkyl vinyl ethers such as methyl vinyl ether, ethyl vinyl ether, propyl vinyl ether, isopropyl vinyl ether, butyl vinyl ether, isobutyl vinyl ether, sec-butyl vinyl ether, tert-butyl vinyl ether, pentyl vinyl ether, hexyl vinyl ether, octyl vinyl ether, decyl vinyl ether and dodecyl vinyl ether; alicyclic vinyl ethers such as cyclopentyl vinyl ether, cyclohexyl vinyl ether, norbornyl vinyl ether, adamantyl vinyl ether and butyrolactone vinyl ether; perfluoroalkyl vinyl ethers such as perfluoromethyl vinyl ether, perfluoroethyl vinyl ether, perfluoropropyl vinyl ether, perfluoroisopropyl vinyl ether, perfluorobutyl vinyl ether, perfluoroisobutyl vinyl ether, perfluoro-sec-butyl vinyl ether, perfluoro-tert-butyl vinyl ether, perfluoropentyl vinyl ether, prefluorohexyl vinyl ether, perfluorooctyl vinyl ether and perfluorododecyl vinyl ether; hydroxyl-containing vinyl ethers such as hydroxymethyl vinyl ether, 2-hydroxyethyl vinyl ether, 3-hydroxypropyl vinyl ether, 4-hydroxybutyl vinyl ether, 5-hydroxypentyl vinyl ether, 6-hydroxyhexyl vinyl ether, diethylene glycol, monovinyl ether, polyethylene glycol monovinyl ether and 1,4-cyclohexanedimethanol vinyl ether; and other vinyl ethers such as ethylhexyl vinyl ether, methoxyethyl vinyl ether, ethoxyethyl vinyl ether, chlorethyl vinyl ether, 1-methyl-2,2-dimethylpropyl vinyl ether, 2-ethylbutyl vinyl ether, diethylene glycol vinyl ether, dimethylaminoethyl vinyl ether, benzyl vinyl ether and tetrahydrofurfuryl vinyl ether.

Examples of the allyl ether are methyl allyl ether, ethyl allyl ether, propyl allyl ether, butyl allyl ether, benzyl allyl ether, cyclohexyl allyl ether and hydroxyl-containing allyl ethers such as alkylene glycol monoallyl ethers e.g. ethylene glycol monoallyl ether, propylene glycol monoallyl ether, diethylene glycol monoallyl ether, polyethylene glycol monoallyl ether, hydroxybutyl allyl ethers and allyl ethers of polyols e.g. glycerin monoallyl ether.

There can also be used: epoxy-containing vinyl ethers and allyl ethers; β-ketoester-containing vinyl ethers and allyl ethers; and silicon-containing vinyl ethers each of which has a hydrolytic group, such as trimethoxysilyl vinyl ether.

Examples of the allyl ester are allyl acetate, allyl caproate, allyl caprylate, allyl laurate, allyl palmitate, allyl stearate, allyl benzoate, allyl acetoacetate and allyl lactate.

Examples of the vinyl ester are vinyl butylate, vinyl isobutylate, vinyl trimethylacetate, vinyl diethylacetate, vinyl valerate, vinyl caproate, vinyl chloracetate, vinyl dichloracetate, vinyl methoxyaceate, vinyl butoxyacetate, vinyl acetoacetate, vinyl lactate, vinyl-β-phenylbutylate and vinyl chlorohexylcarboxylate.

There can also be used: dialkyl itaconates such as dimetyl itaconate, diethyl itaconate and dibutyl itaconate; dialkyl or monoalkyl esters of fumaric acid, such as dibutyl fumarate; and alkyl esters of vinyl aceate, such as ethyl vinyl acetate.

Examples of the olefin or fluorine-containing olefin are ethylene, propylene, cyclohexene, and fluoroolefins such as vinyl fluoride, vinylidene fluoride, trifluoroethylene, chlorotrifluoroethylene, tetrafluoroethylene, hexafluoropropylene, hexafluoroisobutene and octafluorocyclopentene.

The styrenic compound is a compound in which a vinyl group is bonded to an aromatic ring. Examples of the styrenic compound are styrene, m- or p-methoxystyrene, m- or p-ethoxystyrene, m- or p-propoxystyrene, m- or p-isopropoxystyrene, m- or p-butoxystyrene, m- or p-tert-butoxystyrene, m- or p-(1-ethoxyethoxy)styrene, m- or p-(1-ethoxypropoxy)styrene, m- or p-(1-isobutoxyethoxy)styrene, m- or p-(2-tetrahydropyranyloxy)styrene, m- or p-tert-butoxycarbonyloxystyrene, m- or p-acetoxystyrene, m- or p-propionyloxystyrene, m- or p-pivaloyloxystyrene, m- or p-benzoyloxystyrene, m- or p-mesyloxystyrene, m- or p-phenylsulfonyloxystyrene and m- or p-tosyloxystyrene. A halogen atom, an alkyl group or a fluorine-containing alkyl group may be bonded to α-position in each of the above styrenic compounds.

For example, it is feasible in the present invention to introduce a styrenic compound structure to the fluorine-containing polymer compound by copolymerization of p-butoxycarbonyloxystyrene and conversion of a butoxycarbonyl moiety of the copolymer to a hydroxyl group.

The norbonene compound or fluorine-containing norbornene compound is a norbornene monomer having a monocyclic or polycyclic structure. It is preferable to use a norbornene compound obtained by Diels-Alder addition reaction of an unsaturated compound, such as an allyl alcohol, a fluorine-containing allyl alcohol, an acrylic acid, an α-fluoroacrylic acid, a methacrylic acid and any of the acrylic esters, methacrylic esters, fluorine-containing acrylic esters and fluorine-containing methacrylic esters described in the present specification, with cyclopentadiene or cyclohexadiene.

Examples of the acrylic amide or methacrylic amide are unsaturated amides such as acrylamide, methacrylicamide, N-alkyl acrylicamide or methacrylicamide (whose alkyl group is of 1 to 10 carbon atoms, e.g., methyl, ethyl, propyl, butyl, tert-butyl, heptyl, octyl, cyclohexyl or hydroxyethyl), N,N-dialkyl acrylicamide or methacrylicamide (whose alkyl group is of 1 to 10 carbon atoms, e.g., methyl, ethyl, butyl, isobutyl, ethylhexyl or cyclohexyl), N-hydroxyethyl-N-methyl acrylicamide or methacrylicamide, N-methylol acrylicamide or methacrylicamide and diacetone acrylicamide.

There can be used other copolymerization monomers such as acrylic acid, methacrylic acid, vinylsulfonic acid, maleic acid, fumaric acid, crotonic acid, itaconic acid, maleimide, acrylonitrile, methacrylonitrile, maleironitrile, alkoxysilyl-containing vinylsilane and allyloxyethanol.

It is preferable in the fluorine-containing polymer compound of the present invention to use at least one kind of acrylic esters, fluorine-containing acrylic esters, methacrylic esters, fluorine-containing methacrylic esters, styrenic compounds and fluorine-containing styrenic compounds.

There is no particular limitation on the kind of the copolymerization monomer used as long as the monomer is copolymerizable with the fluorine-containing unsaturated carboxylic acid amide. In order to use the resulting resist base resin for exposure to high energy radiation of 300 nm or less wavelength or electron beam radiation, it is preferable that the monomer contains no multiple bond and no aromatic ring.

[Polymerization Method]

There is no particular limitation on the polymerization process for production of the fluorine-containing polymer compound in the present invention. The polymerization reaction can be done by any common polymerization process. It is preferable to adopt radical polymerization process or ionic polymerization process. In some cases, it is feasible to adopt coordination anionic polymerization process, living anionic polymerization process, cationic polymerization process, ring opening metathesis polymerization process, vinylene polymerization process, or vinyl addition process.

The radical polymerization process can be conducted by a known polymerization technique such as bulk polymerization, solution polymerization, suspension polymerization or emulsion polymerization technique in a batch, semi-continuous or continuous operation system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Further, the polymerization reaction can be done by the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; alcohol solvents such as methanol, isopropyl alcohol and ethylene glycol monomethyl ether. Water, ether solvents, cyclic ether solvents, fluorocarbon solvents and aromatic solvents are also usable. These solvents can be used solely or in combination of two or more thereof. A molecular weight adjusting agent such as mercaptan may be used in combination. The reaction temperature of the copolymerization reaction is set as appropriate depending on the kind of the radical polymerization initiator or radical initiating source and is generally preferably in the range of 20 to 200° C., more preferably 30 to 140° C.

The organic solvent or water can be removed from the resulting fluorine-containing polymer solution or dispersion by reprecipitation, filtration, distillation by heating under a reduced pressure or the like.

[Resist Composition]

The fluorine-containing polymer compound is useful to improve the transparency of the resist film when it contains a large number of fluorine atoms and to impart etching resistance and high glass transition temperature to the resist film when it has a ring structure. The fluorine-containing polymer compound of the present invention is thus applicable in different fields.

The fluorine-containing polymer compound of the present invention can be used for a specific purpose depending on the kind of $R^3$ bonded to the end of the side chain of the polymer compound as mentioned above. The polymer compound, when containing as $R^3$ an acid labile group eliminated in the presence of an acid generated from an acid generator by light irradiation so as to change the polymer compound, which has been insoluble in an aqueous alkali solution before the light irradiation, to be soluble in the aqueous alkali solution, can be used as a base resin of a positive resist composition. The polymer compound, when containing as $R^3$ a neutral hydroxyl-containing group that has a neutral hydroxyl group to react with a cross-linking agent in the presence of an acid generated from an acid generator by light irradiation so as to change the polymer compound, which has been soluble in an aqueous alkali solution, to be insoluble or difficult to solve in the aqueous alkali solution, can be used as a base resin of a negative resist composition. When $R^3$ is a hydrogen atom or any organic group other than the acid labile group or neutral hydroxyl-containing group, the polymer compound can be introduced as a repeating unit into a base resin to increase the solubility of the base resin in an unexposed state, or can be used in combination with a base resin to control the solubility of the resist composition.

The chemically amplified resist composition contains not only the base resin but also a photoacid generator and a solvent and may further contain any additive(s) such as a basic compound, a dissolution inhibitor and/or a cross-linking agent.

[Additive Resin]

As the additive resin, there can be used any polymer compound obtained by polymerization of one or two or more selected from the monomers as explained for the repeating unit (b).

[Cross-Linking Agent]

In the negative resist composition, any of known cross-linking agents for chemically amplified negative resist compositions can be selected and used.

More specifically, there can be used as the cross-linking agent any compounds each formed by reacting an amino group-containing compound such as melamine, acetoguanamine, benzoguanamine, urea, ethylene urea, propylene urea or glycoluril, with either formaldehyde or a mixture of formaldehyde and a lower alcohol and thereby substituting a hydrogen atom of the amino group with a hydroxymethyl group or a lower alkoxymethyl group.

Herein, the cross-linking agents formed using melamine, urea, alkylene urea e.g. ethylene urea, propylene urea etc. and glycoluril are referred to as "melamine-based cross-linking agents", "urea-based cross-linking agents", "alkylene urea-based cross-linking agents" and "glycoluril-based cross-linking agents", respectively. The cross-linking agent as the component (C) is preferably at least one selected from the group consisting of melamine-based cross-linking agents, urea-based cross-linking agents, alkylene urea-based cross-linking agents and glycoluril-based cross-linking agents. Particularly preferred is a glycoluril-based cross-linking agent.

Examples of the melamine-based cross-linking agents are hexamethoxymethylmelamine, hexaethoxymethylmelamine, hexapropoxymethylmelamine and hexabutoxymethylmelamine. Among others, hexamethoxymethylmelamine is preferred.

Examples of the urea-based cross-linking agents are bismethoxymethylurea, bisethoxymethylurea, bispropoxymethylurea and bisbutoxymethylurea. Among others, bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

These cross-linking agents can be used solely or in combination of two or more thereof. In the present invention, the total amount of the cross-linking agent in the negative resist composition is preferably 3 to 30 parts by mass, more preferably 3 to 25 parts by mass, most preferably 5 to 20 parts by mass, per 100 parts by mass of the base resin. When the total amount of the cross-linking agent is not less than the above lower limit, the resist composition can form a good resist pattern by sufficient cross-linking. The resist composition can attain good resist solution storage stability and can be prevented from deterioration in sensitivity with time when the total amount of the cross-linking agent is not larger than the above upper limit.

[Basic Compound]

The basic compound is preferably contained as an optional component in the resist composition in the present invention so as to function as a quencher or to obtain improvements in resist pattern profile and post exposure stability.

There can be used any known basic compounds such as primary, secondary and tertiary aliphatic amines, aromatic amines, heterocyclic amines, nitrogen-containing compounds each having a hydroxyphenyl group, alcoholic nitrogen-containing compounds and amide derivatives. Among others, secondary and tertiary apliphatic amines, aromatic amines and heterocyclic amines are preferred.

More specifically, the aliphatic amines includes alkylamines or alkylalcoholamines each formed by replacing at least one hydrogen of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

There can also be used other basic compounds. Other examples of the basic compound are: aromatic or heterocyclic amines such as aniline and aniline derivatives e.g. N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine; heterocyclic amines such as 1,5-diazabicyclo[4.3.0]nona-5-ene, 1,8-diazabicyclo[5.4.0]undeca-7-ene, 1,4-diazabicyclo[2.2.2]octane, 4-dimethylaminopyridine, hexamethylenetetramine and 4,4-dimethylimidazoline; hindered amines such as bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydoxyethyl)morpholine, 2-(2-hydroxyethyl)pyridine, 1-(2-hydroxyethyl)piperazine and 1-[2-(2-hydroxyethoxy)ethyl]piperazine. These compounds can be used solely or in combination of two or more thereof. The amount of the basic compound used is generally 0.01 to 5 parts by mass per 100 parts by mass of the base resin.

In the negative resist resin composition, an organic carboxylic acid or a phosphorus oxo acid or derivative thereof may be contained an optional component in order to prevent sensitivity deterioration caused by the addition of the basic compound and to obtain improvements in resist pattern profile and post exposure stability. These acid compounds can be used solely or in combination with the basic compound. Suitable examples of the organic carboxylic acid are malonic acid, citric acid, malic acid, succinic acid, benzoic acid and salicylic acid.

Suitable examples of the phosphorus oxo acid and derivative thereof are: phosphoric acids and derivatives thereof, such as phosphoric acid, di-n-butyl phosphate and diphenyl phosphate; phosphonic acids and derivatives thereof, such as phosphonic acid, dimethyl phosphonate, di-n-butyl phosphonate, phenylphosphonic acid, diphenyl phosphonate and dibenzyl phosphonate; and phosphinic acids and derivatives thereof, such as phosphinic acid and phenylphosphinic acid. Among others, phosphonic acid is particularly preferred.

[Solvent]

It is feasible in the present invention to form a thin film of the fluorine-containing polymer compound by e.g. dissolving the polymer compound in an organic solvent, applying the polymer solution and drying the coating of the polymer solution. There is no particular limitation on the solvent as long as the fluorine-containing polymer compound can be dissolved in the solvent. Examples of the organic solvent are: ketones such as acetone, methyl ethyl ketone, cyclohexanone, methyl isoamyl ketone and 2-heptanone; polyhydric alcohols and derivatives thereof, such as ethylene glycol, ethylene glycol monoacetate, diethylene glycol, diethylene glycol monoacetate, propylene glycol, propylene glycol monoacetate, propylene glycol monomethyl ether, propylene glycol monomethyl ether acetate (PGMEA), dipropylene glycol, and monomethyl ether, monoethyl ether, monopropyl ether, monobutyl ether or monophenyl ether of dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used solely or in combination of two or more thereof.

[Surfactant]

Preferably, the surfactant, more preferably either one or two or more of fluorine- and/or silicon-based surfactants (fluorine-based surfactants, silicon-based surfactants and surfactant containing both of fluorine and silicon atoms), is contained in the resist composition of the present invention.

The addition of such a surfactant into the resist composition is particularly effective for use by exposure to radiation of 250 nm or less wavelength, notably 200 nm or less wavelength, and for pattern formation with a narrower pattern line width. It is possible to attain good sensitivity and resolution and enable resist patterning with less adhesion and development failures.

[Acid Generator]

In the present invention, a known photoacid generator is usable for the resist composition. As the photoacid generator, there can be used any one selected from photoacid generators for chemically amplified negative resist compositions. Examples of the photoacid generator are bissulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The amount of the photoacid generator used is generally in the range of 0.5 to 20 parts by mass per 100 parts by mass of the resist composition. If the amount of the photoacid generator is less than 0.5 parts by mass, the resin composition unfavorably results in insufficient pattern formation. If the amount of the photoacid generator exceeds 20 parts by mass, it is difficult to prepare a uniform solution from the resin composition. Further, the resin composition unfavorably tends to become low in storage stability.

There is no particular limitation on the additive resin as long as the additive resin is soluble in the solvent used and is compatible with the other components of the resist composition. The additive resin functions as a plasticizer, stabilizer, viscosity improver, leveling agent, antifoaming agent, compatibilizer, primer etc.

[Pattern Formation Method]

The resist composition of the present invention can be applied for resist pattern formation by any conventional photoresist technique. Namely, the solution of the resist composition is first applied to a substrate such as silicon wafer by e.g. a spinner and dried to form a photosensitive film of the resist composition. The photosensitive film is irradiated with high energy radiation of 300 nm or less wavelength or electron beam radiation by e.g. an exposure device through a desired mask pattern, and then, subjected to heating. Subsequently, the photosensitive film is developed with an alkaline developer such as 0.1 to 1 mass % tetramethylammonium hydroxide solution. It is possible by the above pattern formation method to form a resist pattern according to the mask pattern. As mentioned above, various miscible additives, such as additional resin, quencher, plasticizer, stabilizer, coloring agent, surfactant, viscosity improver, leveling agent, antifoaming agent, compatibilizer, primer and antioxidant, may be added to the resist material as desired.

There is no particular limitation on the high energy radiation used in the present invention. In the case of fine patterning, it is particularly effective to use high energy radiation of 300 nm or less wavelength, such as near-ultraviolet radiation (wavelength: 380 to 200 nm) or vacuum-ultraviolet radiation (far-ultraviolet radiation, VUV, wavelength: 200 to 10 nm) produced by a KrF excimer laser, ArF excimer laser etc., far-ultraviolet radiation (EUV, wavelength: 10 nm or less) such as synchrotron radiation, DPP (Discharge Produced Plasma) or LPP (Laser Produced Plasma), soft X-ray, X-ray or γ-ray produced by synchrotron radiation, or electron beam radiation. Herein, soft X-ray of 13.5 nm wavelength used for photolithography may be included in EUV according to conventional practice in the field of the present invention. It is also effective in the pattern formation method of the present invention to use an exposure device that has a generation source of the high energy radiation of 300 nm or less wavelength or electron beam. There can also be used a liquid immersion exposure device that uses a medium with less absorption of high energy radiation used and enables more efficient fine patterning in terms of numerical aperture and effective wavelength. The resist composition of the present invention can suitably be applied to such an exposure device.

EXAMPLES

The present invention will be described in more detail below by way of the following examples. It is herein noted that the following examples are illustrative and are not intended to limit the present invention thereto.

Example 1-1

Preparation of 2,2-difluoro-3-hydroxy-pentanoic acid ethyl ester

[Chem. 40]

Into a 2-L glass flask with a dropping funnel and a condenser, 70.6 g (1.08 mol/1.1 eq) of activated zinc metal and 300 mL of tetrahydrofuran (THF, dehydrated) were added. An ethyl bromodifluoroacetate/THF solution (prepared by dissolving 200 g (0.985 mol) of ethyl bromodifluoroacetate into 80 mL of THF (dehydrated)) and a propionaldehyde/THF solution (prepared by dissolving 58.7 g (1.01 mol/1.0 eq) of propionaldehyde in 80 mL of THF (dehydrated)) were simultaneously dropped into the glass flask. The resulting solution was stirred for 2 hours at room temperature. The completion of the reaction was confirmed by gas chromatography. After that, the solution was separated into an organic layer and an aqueous layer with the addition of water and diisopropyl ether. The thus-obtained organic layer was washed with diluted hydrochloric acid and with water, dried, concentrated under a reduced pressure, and then, distilled under a reduced pressure. With this, 110 g of 2,2-difluoro-3-hydroxy-pentanoic acid ethyl ester was obtained as a light-brown oily substance (yield: 60%, purity: 98%).

Properties of 2,2-difluoro-3-hydroxy-pentanoic acid ethyl ester $^1$H NMR (measurement solvent: deuterium chloroform, reference material: tetramethylsilane) δ=4.33 (t, J=7.6 Hz, 3H; CH$_2$ of O—CH$_2$CH$_3$), 3.89 (m, 1H; CH of CH—OH), 2.06 (d, J=7.2 Hz, 1H; OH of CH—OH), 1.74 (m, 1H; CH$_2$ of C—CH$_2$CH$_3$), 1.54 (m, 1H; CH$_2$ of C—CH$_2$CH$_3$), 1.32 (t, J=7.6 Hz, 3H; CH$_3$ of C—CH$_2$CH$_3$), 1.02 (t, J=7.6 Hz, 3H; CH$_3$ of O—CH$_2$CH$_3$).

$^{19}$F NMR (measurement solvent: deuterium chloroform, reference material: trichlorofluoromethane) δ=−115.33 (d, J=265 Hz, 1F), −122.88 (d, J=265 Hz, 1F).

Example 1-2

Preparation of 2,2-difluoro-3-hydroxy-pentanoic acid

[Chem. 41]

Into a 10-L glass flask with a dropping funnel, 784 g (purity: 98%, 4.30 mol) of 2,2-difluoro-3-hydroxy-pentanoic acid ethyl ester, 300 mL of methanol and 2400 mL of water were added. The glass flask was cooled with ice water, followed by dropping 515 g (6.18 mol/1.4 eq) of 48% aqueous sodium hydroxide solution into the glass flask over 2 hours. The resulting solution was heated to room temperature and stirred for 1 hour. The completion of the reaction was confirmed by gas chromatography. The solution was washed twice with 800 mL of diisopropyl ether. The glass flask was again cooled with ice water. Then, 717 g (6.88 mmol/1.6 eq) of concentrated hydrochloric acid was dropped into the glass flask. After confirming that the pH of the solution was 1, the solution was stirred for 1 hour at room temperature. Subsequently, the solution was separated into an organic layer and an aqueous layer with the addition of 1000 mL of a mixed solution of diisopropyl ether and ethyl acetate. The aqueous layer was extracted three times with 1000 mL of a mixed solution of diisopropyl ether and ethyl acetate. The thus-obtained organic layers were combined and concentrated under a reduced pressure. With this, 683 g of 2,2-difluoro-3-hydroxy-pentanoic acid was obtained (yield: 98%, purity: 95%).

Properties of 2,2-difluoro-3-hydroxy-pentanoic acid $^1$H NMR (measurement solvent: deuterium dimethyl sulfoxide, reference material: tetramethylsilane) δ=3.72 (m, 1H; CH of CH—OH), 1.52 (m, 1H; CH$_2$ of CH—CH$_2$CH$_3$), 1.39 (m, 1H; CH$_2$ of CH—CH$_2$CH$_3$), 0.92 (t, J=7.6 Hz, 3H; CH$_3$ of CH—CH$_2$CH$_3$).

$^{19}$F NMR (measurement solvent: deuterium dimethyl sulfoxide, reference material: trichlorofluoromethane) δ=−113.90 (d, J=250 Hz, 1F), −121.01 (d, J=250 Hz, 1F).

Example 1-3

Preparation of methacrylic acid 1-hydroxycarbonyl-1,1-difluoro-2-butyl ester

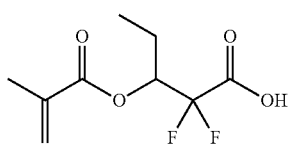

[Chem. 42]

Into a 3-L glass flask with a dropping funnel, 295 g (purity: 95%, 1.82 mol) of 2,2-difluoro-3-hydroxy-pentanoic acid, 910 g of acetonitrile, 35 g (0.364 mol/0.2 eq) of methanesulfonic acid and 1 g of antioxidant "NONFLEX MBP" (manufactured by Seiko Chemical Co., Ltd.) were added. Subsequently, 470 g (3.05 mol/1.7 eq) of previously-distilled methacrylic anhydride was dropped into the glass flask at room temperature. The resulting solution was heated to 50° C. and stirred for 2 hours. The completion of the reaction was confirmed by $^{19}$F NMR. After that, the solution was separated into an organic layer and an aqueous layer with the addition of 1 L of ethyl acetate and 1 L of water. The organic layer was admixed with an aqueous saturated sodium hydrogencarbonate solution until the pH of the mixed solution became 6. The mixed solution was then separated into an organic layer and an aqueous layer. The organic layer was washed twice with 1 L of water. The thus-obtained aqueous layers were combined and admixed with 15% HCl until the pH of the mixed solution became 1. The solution was separated into an organic layer and an aqueous layer with the addition of 1 L of a mixed solution of diisopropyl ether/ethyl acetate. The aqueous layer was extracted three times with 1 L of a mixed solution of diisopropyl ether/ethyl acetate. The thus-obtained organic layers were combined, dried and concentrated under a reduced pressure. With this, 722 g of methacrylic acid 1-hydroxycarbonyl-1,1-difluoro-2-butyl ester was obtained (yield: 87%, purity: 56%).

Properties of methacrylic acid 1-hydroxycarbonyl-1,1-difluoro-2-butyl ester $^1$H NMR (measurement solvent: deuterium chloroform, reference material: tetramethylsilane) δ=6.10 (s, 1H; =CH$_2$), 5.55 (s, 1H; =CH$_2$), 5.39 (m, 1H; CH—OH), 1.85 (s, 3H; CH$_3$—C), 1.73 (m, 2H; CH$_2$ of CH—CH$_2$CH$_3$), 0.87 (t, J=7.6 Hz, 3H; CH$_3$ of CH—CH$_2$CH$_3$).

$^{19}$F NMR (measurement solvent: deuterium chloroform, reference material: trichlorofluoromethane) δ=−114.54 (d, J=279 Hz, 1F), −119.40 (d, J=279 Hz, 1F).

Example 2

Preparation of methacrylic acid 1-chlorocarbonyl-1,1-difluoro-2-butyl ester

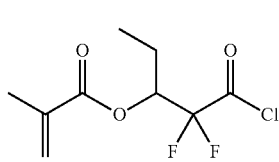

[Chem. 43]

Into a 3-L vessel with a dropping funnel, added were 420 g (purity 56%, 1.25 mol) of methacrylic acid 1-hydroxycarbonyl-1,1-difluoro-2-butyl ester obtained in Example 1-3 and 7.50 g (0.11 mol/0.01 eq) of dimethylformamide. Then, 452 g (3.79 mol/0.01 eq) of thienyl chloride were dropped into the vessel at room temperature. The resulting solution was heated to 75° C. and stirred for 4 hours. The completion of the reaction was confirmed by $^{19}$F NMR. After that, the solution was distillated under a reduced pressure. With this, 255 g of methacrylic acid 1-chlorocarbonyl-1,1-difluoro-2-butyl ester was obtained (yield: 92%, purity: 98%).

Properties of methacrylic acid 1-chlorocarbonyl-1,1-difluoro-2-butyl ester $^1$NMR (measurement solvent: deuterium chloroform, reference material: tetramethylsilane) δ=6.14 (s, 1H; =CH$_2$), 5.63 (s, 1H; =CH$_2$), 5.43 (m, 1H; CH—O), 1.92 (s, 3H; CH$_3$—C), 1.82 (m, 2H; CH$_2$ of CH—CH$_2$CH$_3$), 0.96 (t, J=7.6 Hz, 3H; CH$_3$ of CH—CH$_2$CH$_3$).

$^{19}$F NMR (measurement solvent: deuterium chloroform, reference material: trichlorofluoromethane) δ=−108.10 (d, J=259 Hz, 1F), −114.01 (d, J=259 Hz, 1F).

Example 3

Preparation of methacrylic acid 1-aminocarbonyl-1,1-difluoro-2-butyl ester

[Chem. 44]

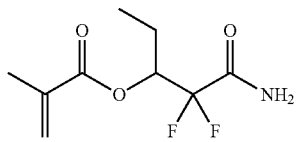

In a 25-mL glass flask with a dropping funnel, 5.0 g (82.2 mmol/4.0 eq) of 28% aqueous ammonia solution was added and stirred. Subsequently, 5.0 g (purity: 98%, 20.4 mmol) of methacrylic acid 1-chlorocarbonyl-1,1-difluoro-2-butyl ester was dropped into the glass flask. The resulting solution was stirred for 10 minutes at room temperature. The completion of the reaction was confirmed by $^{19}$F NMR. After that, the solution was separated into an organic layer and an aqueous layer with the addition of 5 mL of water and 5 mL of diisopropyl ether. The thus-obtained aqueous layer was concentrated under a reduced pressure. With this, 4.1 g of methacrylic acid 1-aminocarbonyl-1,1-difluoro-2-butyl ester was obtained as a white crystalline substance (yield: 86%, purity: 96%).

Properties of methacrylic acid 1-aminocarbonyl-1,1-difluoro-2-butyl ester $^1$H NMR (measurement solvent: deuterium chloroform, reference material: tetramethylsilane) δ=6.40 (br, 1H; NH$_2$), 6.34 (br, 1H; NH$_2$), 6.14 (s, 1H; =CH$_2$), 5.61 (s, 1H; =CH$_2$), 5.42 (m, 1H; CH—O), 1.93 (s, 3H; CH$_3$—C), 1.83 (m, 2H; CH$_2$ of CH—CH$_2$CH$_3$), 0.94 (t, J=7.6 Hz, 3H; CH$_3$ of CH—CH$_2$CH$_3$).

$^{19}$F NMR (measurement solvent: deuterium chloroform, reference material: trichlorofluoromethane) δ=−114.98 (d, J=259 Hz, 1F), −118.38 (d, J=259 Hz, 1F).

Example 4

Preparation of methacrylic acid 3-hydroxypropaneaminocarbonyl-1,1-difluoro-2-butyl ester

[Chem. 45]

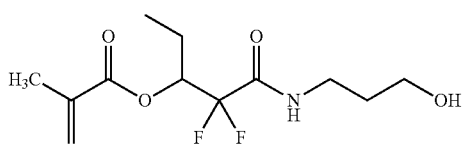

In a 50-mL glass flask with a dropping funnel, 900 mg (12.0 mmol/1.4 eq) of 3-aminopropanol and 8 mL of ethyl acetate were added and stirred. Subsequently, 2.0 g (8.3 mmol) of methacrylic acid 1-chlorocarbonyl-1,1-difluoro-2-butyl ester was dropped into the glass flask. The resulting solution was stirred for 1 hour at room temperature. The completion of the reaction was confirmed by $^{19}$F NMR. After that, the two-layered reaction solution was separated. The obtained upper organic layer was concentrated under a reduced pressure. With this, 2.2 g of methacrylic acid 3-hydroxypropaneaminocarbonyl-1,1-difluoro-2-butyl ester was obtained as a colorless oily substance (yield: 77%, purity: 80%).

Properties of Methacrylic Acid 3-hydroxypropaneaminocarbonyl-1,1-difluoro-2-butyl ester $^1$H NMR (measurement solvent: deuterium chloroform, reference material: tetramethylsilane) δ=6.09 (s, 1H; =CH$_2$), 5.57 (s, 1H; =CH$_2$), 5.38 (m, 1H; CH—O), 3.63 (t, J=6.0 Hz, 2H; CH$_2$ of CH$_2$—OH), 3.44 (q, J=6.0 Hz, 2H; CH$_2$ of NH—CH$_2$), 1.88 (s, 3H; CH$_3$—C), 1.72 (m, 2H; CH$_2$ of CH—CH$_2$CH$_3$), 1.69 (m, 2H; middle CH$_2$ of CH$_2$—CH$_2$—CH$_2$), 0.90 (t, J=7.6 Hz, 3H; CH$_3$ of CH—CH$_2$CH$_3$).

$^{19}$F NMR (measurement solvent: deuterium chloroform, reference material: trichlorofluoromethane) δ=−115.45 (d, J=259 Hz, 1F), −118.98 (d, J=259 Hz, 1F).

Example 5

Preparation of methacrylic acid 1-tert-butylaminocarbonyl-1,1-difluoro-2-butyl ester

[Chem. 46]

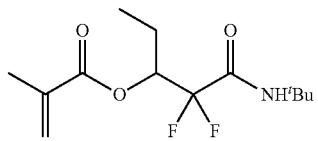

In a 50-mL glass flask with a dropping funnel, 3.0 g (41.6 mmol/2.0 eq) of tertiary butylamine and 5.0 g of diisopropyl ether were added and stirred. Subsequently, 5.0 g (20.8 mmol) of methacrylic acid 1-chlorocarbonyl-1,1-difluoro-2-butyl ester was dropped into the glass flask. The resulting solution was stirred for 10 minutes at room temperature. The completion of the reaction was confirmed by $^{19}$F NMR. After that, the solution was separated into an organic layer and an aqueous layer with the addition of 10 mL of water and 5 mL of diisopropyl ether. The thus-obtained organic layer was concentrated under a reduced pressure. With this, 6.5 g of methacrylic acid 1-tert-butylaminocarbonyl-1,1-difluoro-2-butyl ester was obtained as a white crystalline substance (yield: 99%, purity: 88%).

Properties of methacrylic acid 1-tert-butylaminocarbonyl-1,1-difluoro-2-butyl ester $^1$H NMR (measurement solvent: deuterium chloroform, reference material: tetramethylsilane) δ=6.07 (br, 2H; NH$_2$), 6.07 (s, 1H; =CH$_2$), 5.55 (s, 1H; =CH$_2$), 5.35 (m, 1H;

CH—O), 1.87 (s, 3H; CH$_3$—C), 1.72 (m, 2H; CH$_2$ of CH—CH$_2$CH$_3$), 1.29 (s, 9H; tBu), 0.87 (t, J=7.6 Hz, 3H; CH$_3$ of CH—CH$_2$CH$_3$).

$^{19}$F NMR (measurement solvent: deuterium chloroform, reference material: trichlorofluoromethane) δ=−114.79 (d, J=256 Hz, 1F), −118.97 (d, J=256 Hz, 1F).

Example 6

Production of Fluorine-Containing Polymer Compound (1)

Into a glass flask with a condenser, 1.8 g of methacrylic acid 1-aminocarbonyl-1,1-difluoro-2-butyl ester, 4.5 g of methacrylic acid 3-hydroxy-1-adamantyl ester (MA-HMA, manufactured by Daicel Chemical Industries. Ltd.), 0.1 g of azobisbutyronitrile and 15 mL of methyl ethyl ketone were added. The inside of the glass flask was changed to a nitrogen atmosphere. The resulting solution was heated to 60° C. and stirred for 18 hours. After the completion of the reaction, the solution was admixed with 60 ml of n-hexane and stirred to thereby form a precipitate. The precipitate was taken out of the solution and dried for 20 hours at 55° C. With this, 4.6 g of a fluorine-containing polymer compound (1) was obtained as a white solid substance (yield: 70%). The constitutional ratio of the repeating units of the polymer compound was determined by NMR. The molecular weight of the polymer compound was determined by gel permeation chromatography (GPC, reference material: polystyrene). The test results are indicated in TABLE 1.

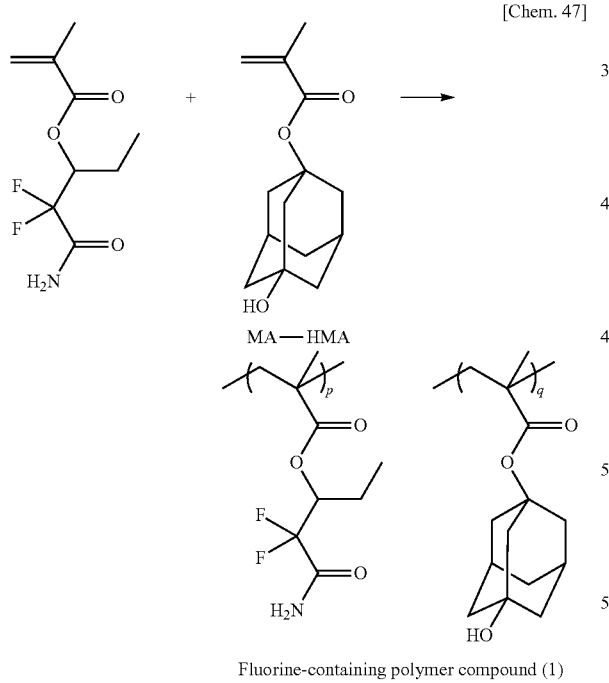

[Chem. 47]

Fluorine-containing polymer compound (1)

Example 7

Production of Fluorine-Containing Polymer Compound (2)

A fluorine-containing polymer compound (2) was produced in the same manner as in Example 6 using methacrylic acid 1-aminocarbonyl-1,1-difluoro-2-butyl ester, methacrylic acid-(2-trifluoromethyl-2-hydroxyl-3,3,3-trifluoropropyl)-norbornanyl ester (MA-BTHB-NB) prepared by a preparation process described in Japanese Laid-Open Patent Publication No. 2004-175740 and MA-HMA. The test results are indicated in TABLE 1.

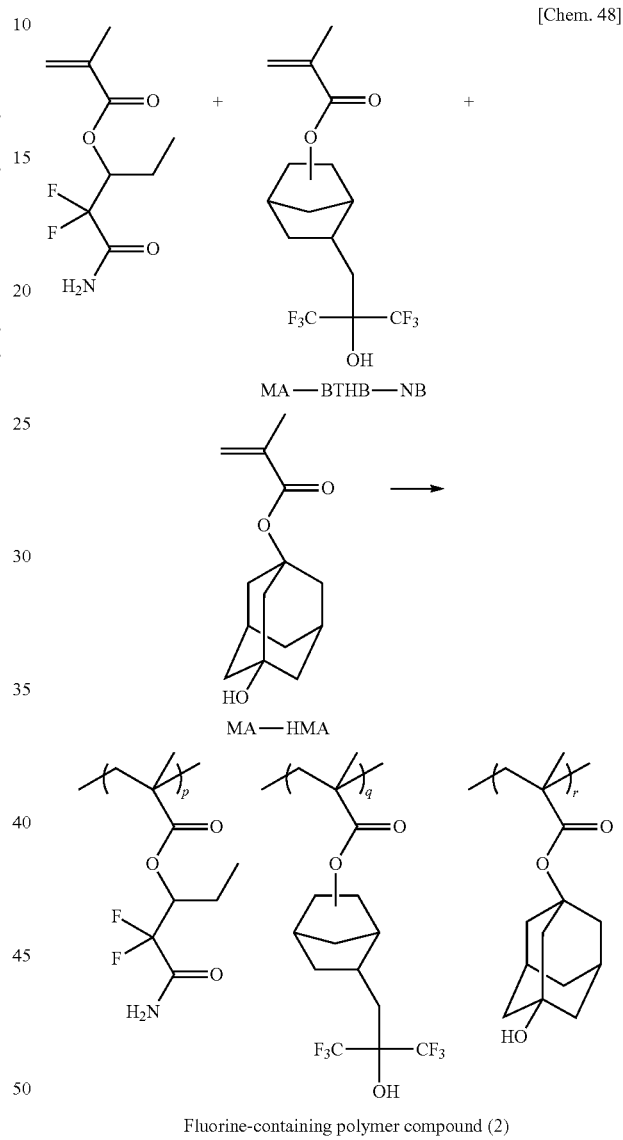

[Chem. 48]

Fluorine-containing polymer compound (2)

Example 8

Production of Fluorine-Containing Polymer Compound (3)

A fluorine-containing polymer compound (3) was produced in the same manner as in Example 6 using methacrylic acid 1-aminocarbonyl-1,1-difluoro-2-butyl ester, MA-HMA and methacrylic acid-2-hydroxyethyl ester (HEMA, manufactured by Tokyo Chemical Industry Co., Ltd.). The test results are indicated in TABLE 1.

[Chem. 49]

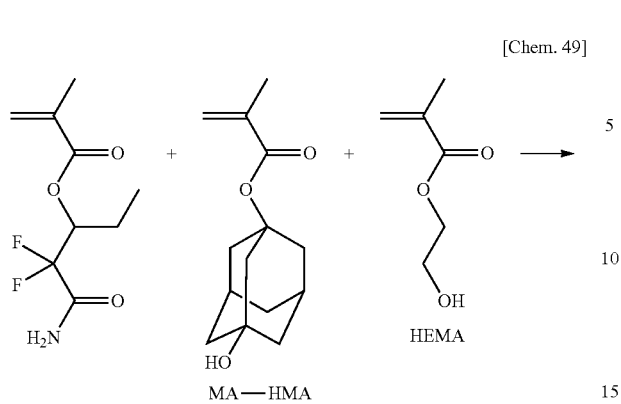

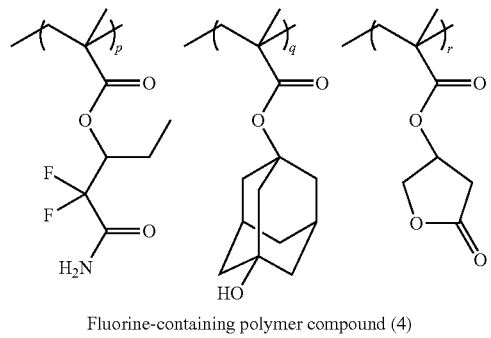

Fluorine-containing polymer compound (4)

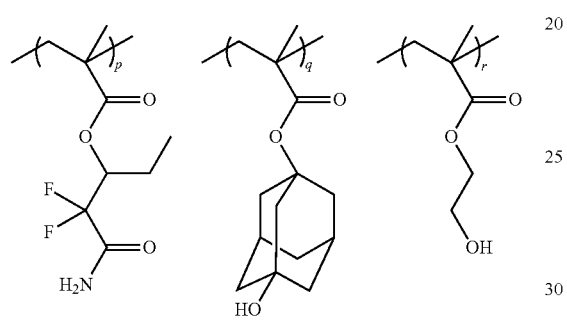

Fluorine-containing polymer compound (3)

Example 9

Production of Fluorine-Containing Polymer Compound (4)

A fluorine-containing polymer compound (4) was produced in the same manner as in Example 6 using methacrylic acid 1-aminocarbonyl-1,1-difluoro-2-butyl ester, MA-HMA and MA-lactone (γ-butyrolactone methacrylate, manufactured by Osaka Organic Chemical Industry Ltd.). The test results are indicated in TABLE 1.

[Chem. 50]

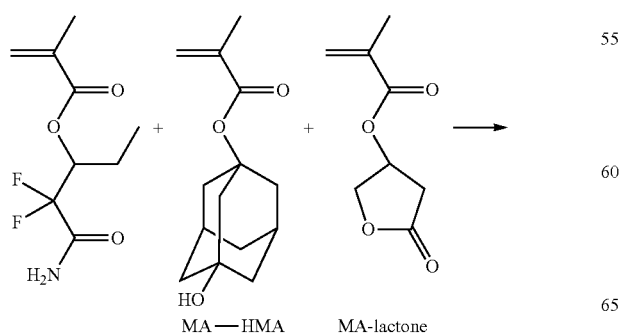

Example 10

Production of Fluorine-Containing Polymer Compound (5)

A fluorine-containing polymer compound (5) was produced in the same manner as in Example 6 using methacrylic acid 1-aminocarbonyl-1,1-difluoro-2-butyl ester, MA-HMA, 5-methacryloyloxy-2,6-norbomane carbolactone (MA-NBL, manufactured by Daicel Chemical Industries. Ltd.) and MA-BTHB-NB. The test results are indicated in TABLE 1.

[Chem. 51]

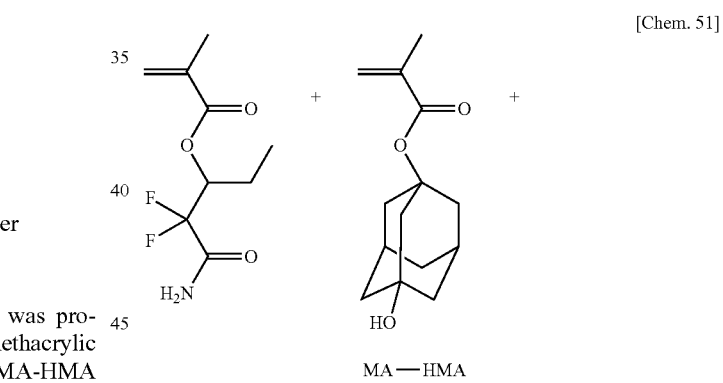

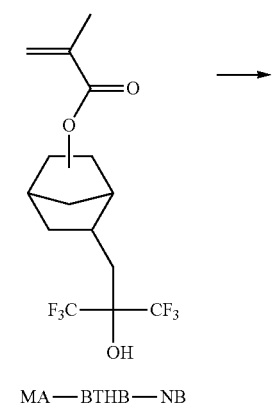

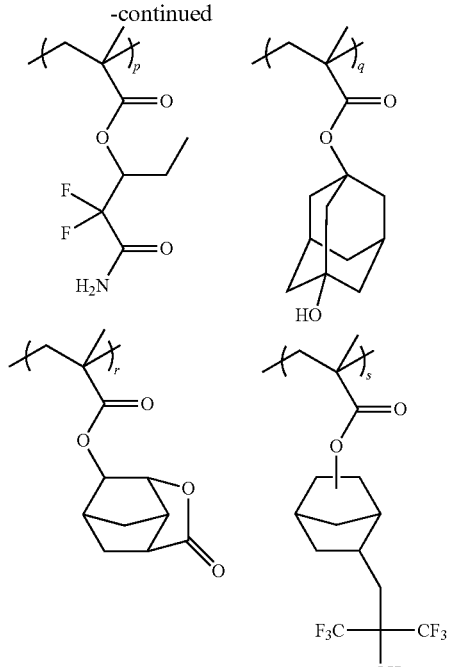

Fluroine-containing polymer compound (5)

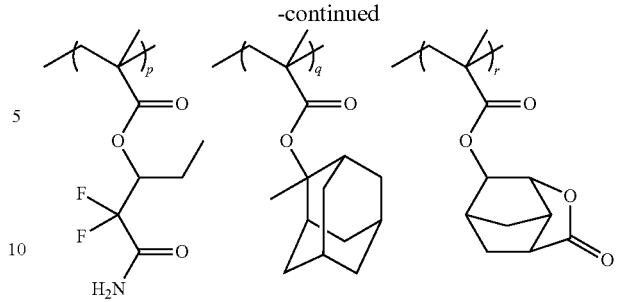

Fluorine-containing polymer compound (6)

Example 11

Production of Fluorine-Containing Polymer Compound (6)

A fluorine-containing polymer compound (6) was produced in the same manner as in Example 6 using methacrylic acid 1-aminocarbonyl-1,1-difluoro-2-butyl ester, methacrylic acid 2-methyl-2-adamantyl ester (MA-MAD) and MA-NBL. The test results are indicated in TABLE 1.

[Chem. 52]

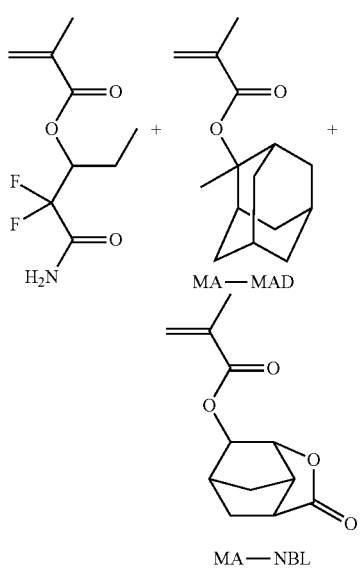

Example 12

Production of Fluorine-Containing Polymer Compound (7)

A fluorine-containing polymer compound (7) was produced in the same manner as in Example 6 using methacrylic acid 1-aminocarbonyl-1,1-difluoro-2-butyl ester, MA-HMA, MA-MAD and MA-NBL. The test results are indicated in TABLE 1.

[Chem. 53]

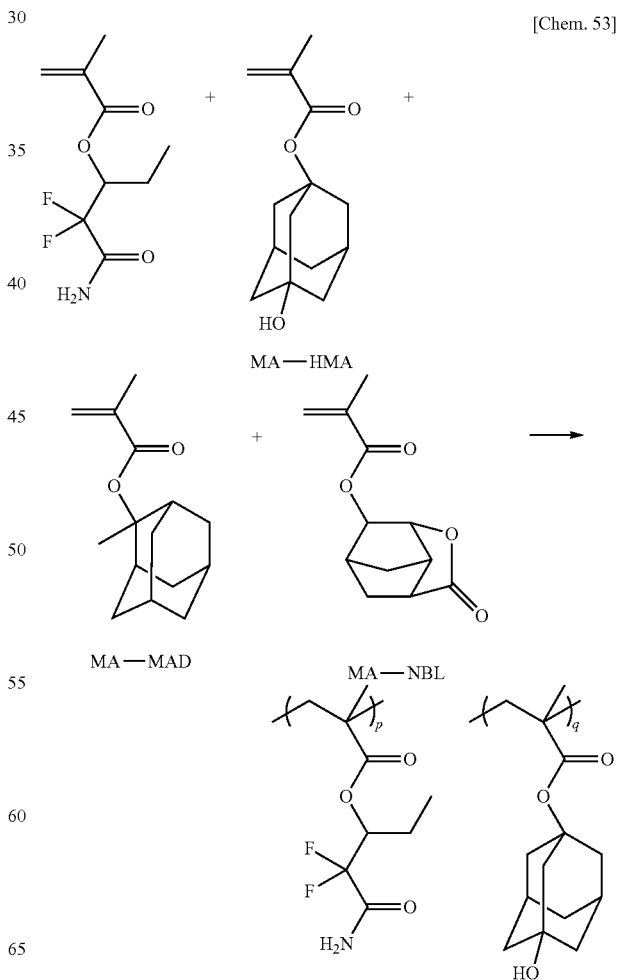

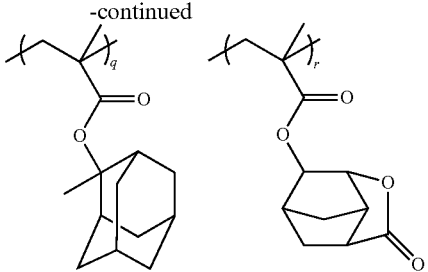

Fluroine-containing polymer compound (7)

Example 13

Production of Fluorine-Containing Polymer Compound (8)

A fluorine-containing polymer compound (8) was produced in the same manner as in Example 6 using methacrylic acid 1-aminocarbonyl-1,1-difluoro-2-butyl ester, methacrylic acid tert-butyl ester and MA-HMA. The test results are indicated in TABLE 1.

[Chem. 54]

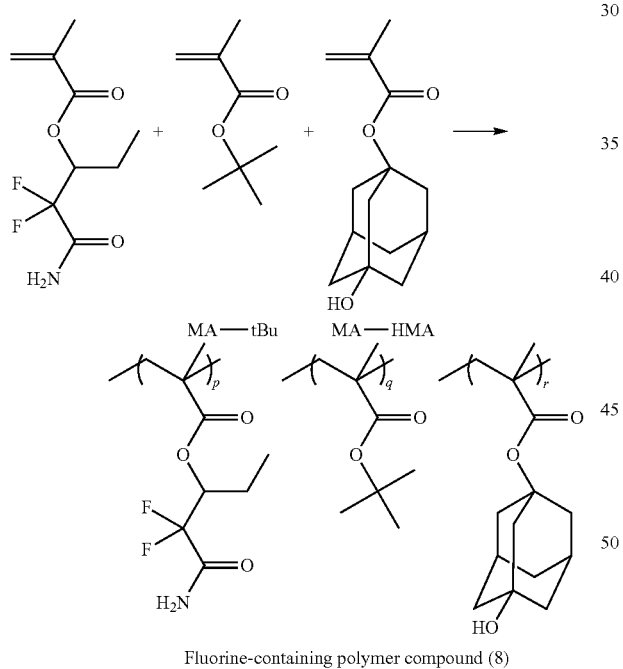

Fluorine-containing polymer compound (8)

Example 14

Production of Fluorine-Containing Polymer Compound (9)

A fluorine-containing polymer compound (9) was produced in the same manner as in Example 6 using methacrylic acid 1-tert-butylaminocarbonyl-1,1-difluoro-2-butyl ester, MA-HMA and MA-lactone. The test results are indicated in TABLE 1.

[Chem. 55]

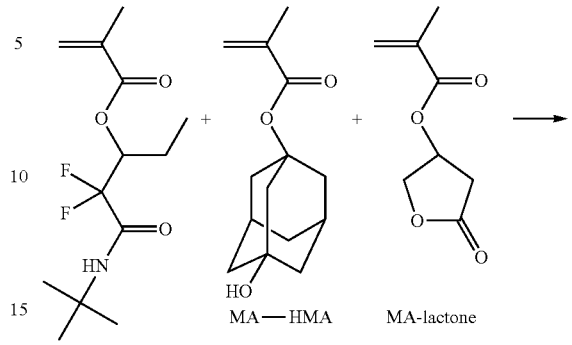

Fluorine-containing polymer compound (9)

Example 15

Production of Fluorine-Containing Polymer Compound (10)

A fluorine-containing polymer compound (10) was produced in the same manner as in Example 6 using methacrylic acid 1-tert-butylaminocarbonyl-1,1-difluoro-2-butyl ester, methacrylic acid 3,5-bis(hexafluoro-2-hydroxy-2-propyl)cyclohexyl ester (MA-3,5-HFA-CHOH) and MA-lactone. The test results are indicated in TABLE 1.

[Chem. 56]

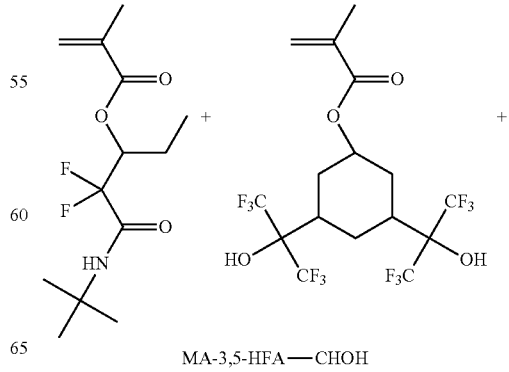

MA-3,5-HFA—CHOH

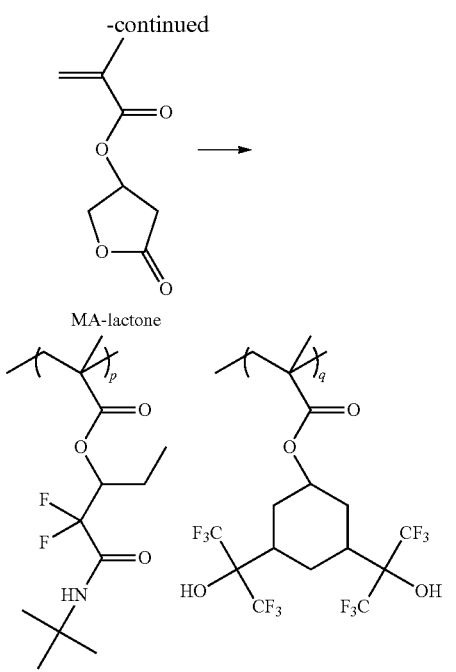

Fluorine-containing polymer compound (10)

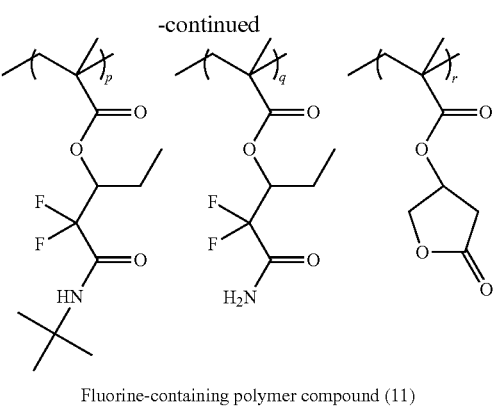

Fluorine-containing polymer compound (11)

Example 16

Production of Fluorine-Containing Polymer Compound (11)

A fluorine-containing polymer compound (11) was produced in the same manner as in Example 6 using methacrylic acid 1-tert-butylaminocarbonyl-1,1-difluoro-2-butyl ester, methacrylic acid 1-aminocarbonyl-1,1-difluoro-2-butyl ester, MA-HMA and MA-lactone. The test results are indicated in TABLE 1.

[Chem. 57]

Example 17

Production of Fluorine-Containing Polymer Compound (12)

A fluorine-containing polymer compound (12) was produced in the same manner as in Example 6 using methacrylic acid 3-hydroxypropaneaminocarbonyl-1,1-difluoro-2-butyl ester, MA-HMA and methacrylic acid (MA). The test results are indicated in TABLE 1.

[Chem. 58]

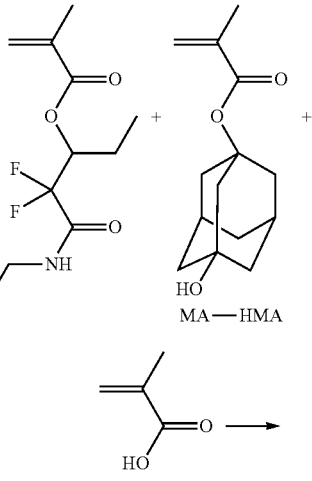

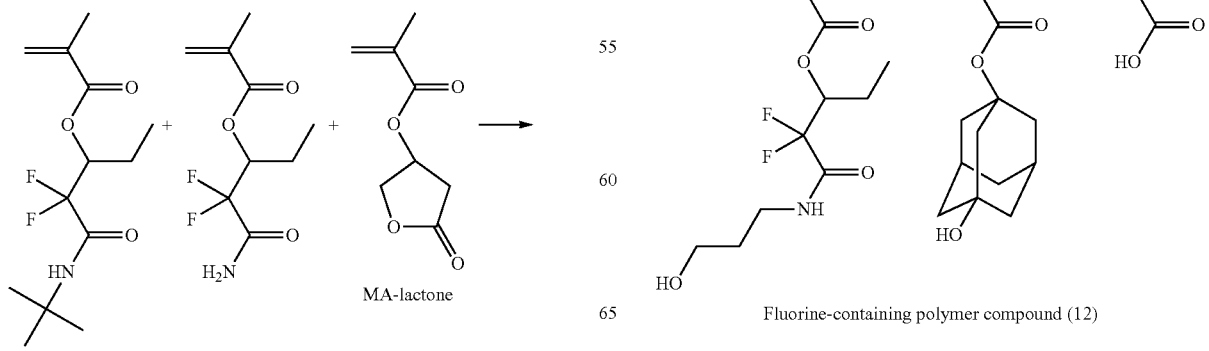

Fluorine-containing polymer compound (12)

Example 18

Production of Fluorine-Containing Polymer Compound (13)

A fluorine-containing polymer compound (13) was produced in the same manner as in Example 6 using methacrylic acid 3-hydroxypropaneaminocarbonyl-1,1-difluoro-2-butyl ester, MA-HMA, methacrylic acid-(2-trifluoromethyl-2-hydroxyl-3,3,3-trifluoropropyl)-norbornanyl ester (A-BTHB-NB) and MA-NBL. The test results are indicated in TABLE 1.

[Chem. 59]

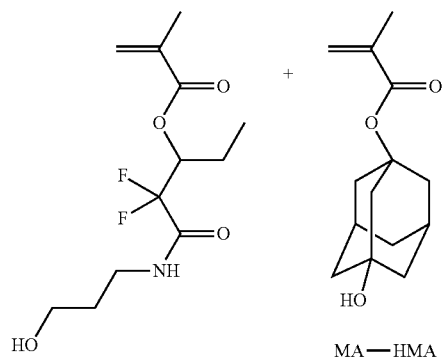

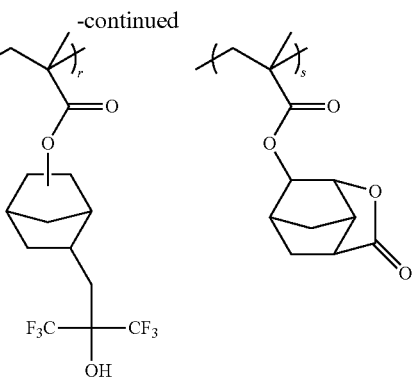

Fluroine-containing polymer compound (13)

Example 19

Production of Fluorine-Containing Polymer Compound (14)

A fluorine-containing polymer compound (14) was produced in the same manner as in Example 6 using methacrylic acid 3-hydroxypropaneaminocarbonyl-1,1-difluoro-2-butyl ester, methacrylic acid 1-aminocarbonyl-1,1-difluoro-2-butyl ester, MA-BTHB-NB and MA-lactone. The test results are indicated in TABLE 1.

[Chem. 60]

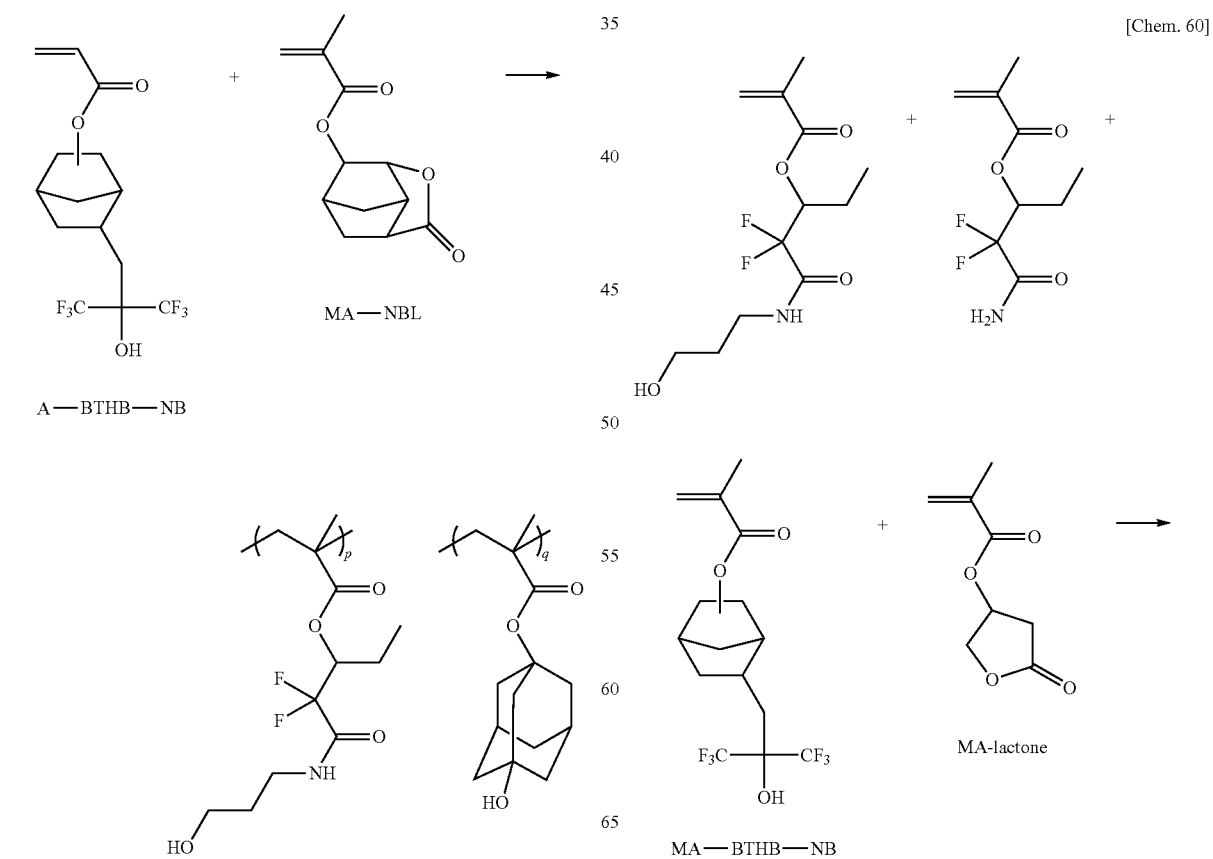

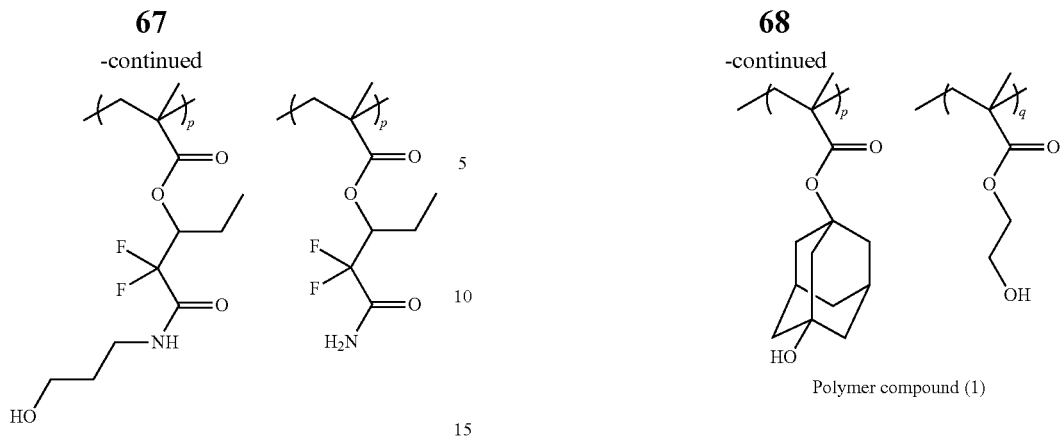

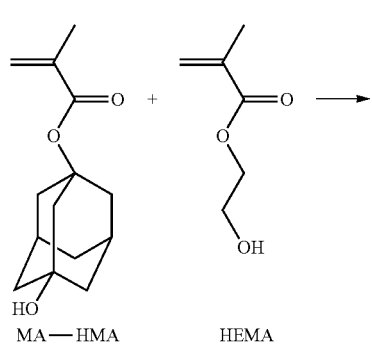

Fluroine-containing polymer compound (14)

Comparative Example 1

Production of Polymer Compound (1)

A polymer compound (1) was produced in the same manner as in Example 6 using MA-HMA and HEMA. The test results are indicated in TABLE 1.

[Chem. 61]

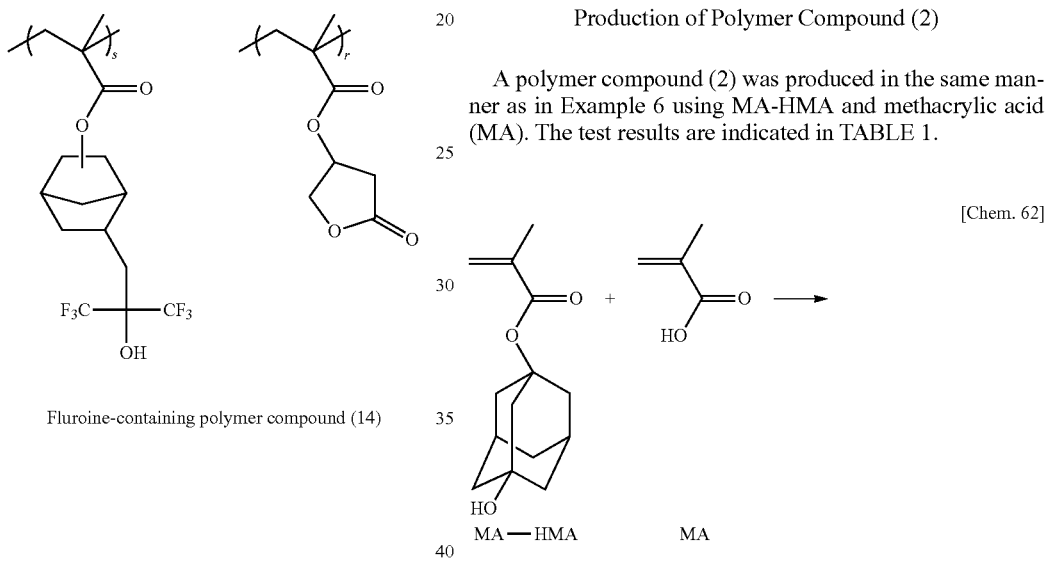

Polymer compound (1)

Comparative Example 2

Production of Polymer Compound (2)

A polymer compound (2) was produced in the same manner as in Example 6 using MA-HMA and methacrylic acid (MA). The test results are indicated in TABLE 1.

[Chem. 62]

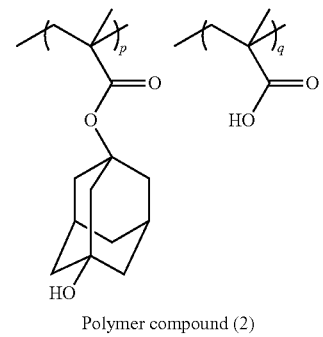

Polymer compound (2)

Comparative Example 3

Production of Polymer Compound (3)

A polymer compound (3) was produced in the same manner as in Example 6 using HEMA, methacrylic acid (MA) and MA-NBL. The test results are indicated in TABLE 1.

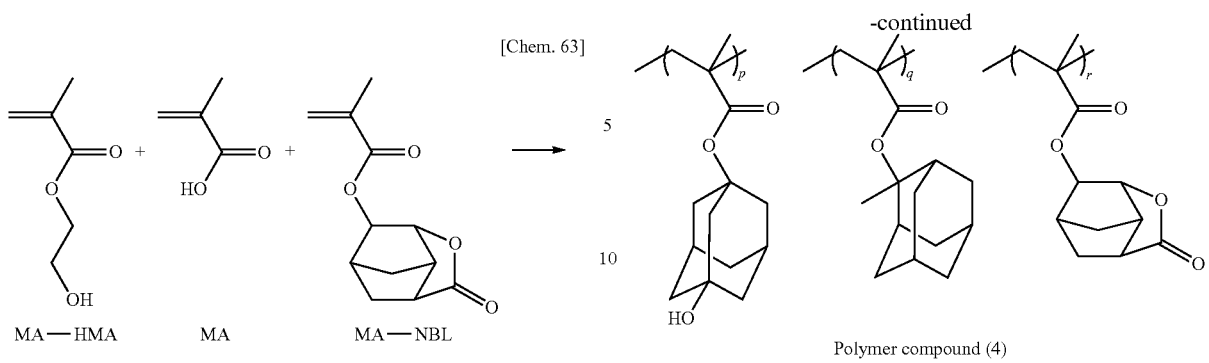

[Chem. 63]

Polymer compound (3)

Comparative Example 4

Production of Polymer Compound (4)

A polymer compound (4) was produced in the same manner as in Example 6 using MA-HMA, MA-MAD and MA-NBL. The test results are indicated in TABLE 1.

[Chem. 64]

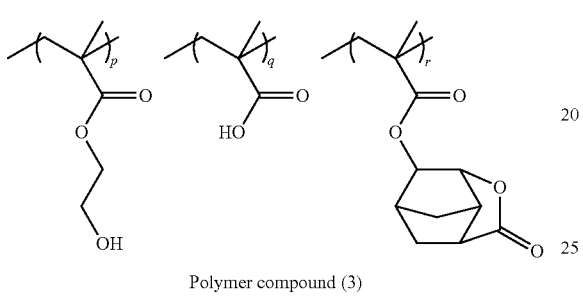

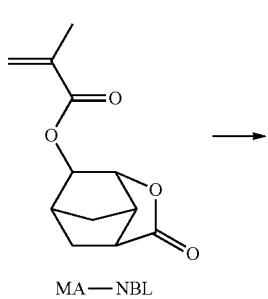

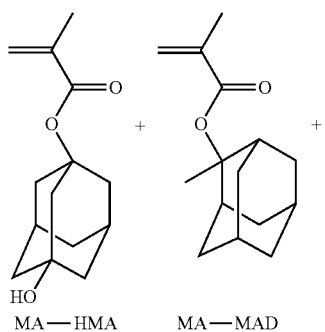

Polymer compound (4)

Comparative Example 5

Production of Polymer Compound (5)

A polymer compound (5) was produced in the same manner as in Example 6 using methacrylic acid tert-butyl ester and MA-HMA. The test results are indicated in TABLE 1.

[Chem. 65]

TABLE 1

| Example/Comparative Example | Polymer compound | Composition (p/q/r/s) | Mw (Mw/Mn) |
|---|---|---|---|
| Example 6 | Fluorine-containing polymer compound (1) | 41/59 | 16900 (2.01) |
| Example 7 | Fluorine-containing polymer compound (2) | 35/29/36 | 16100 (1.82) |
| Example 8 | Fluorine-containing polymer compound (3) | 33/29/38 | 15200 (1.79) |
| Example 9 | Fluorine-containing polymer compound (4) | 28/40/32 | 10100 (1.75) |
| Example 10 | Fluorine-containing polymer compound (5) | 39/34/14/13 | 10900 (1.92) |

TABLE 1-continued

| Example/Comparative Example | Polymer compound | Composition (p/q/r/s) | Mw (Mw/Mn) |
|---|---|---|---|
| Example 11 | Fluorine-containing polymer compound (6) | 33/35/32 | 15200 (2.02) |
| Example 12 | Fluorine-containing polymer compound (7) | 20/28/24/28 | 16500 (1.95) |
| Example 13 | Fluorine-containing polymer compound (8) | 33/41/26 | 14400 (1.83) |
| Example 14 | Fluorine-containing polymer compound (9) | 37/32/31 | 14800 (1.92) |
| Example 15 | Fluorine-containing polymer compound (10) | 37/31/32 | 14900 (1.73) |
| Example 16 | Fluorine-containing polymer compound (11) | 40/24/36 | 15900 (2.09) |
| Example 17 | Fluorine-containing polymer compound (12) | 20/25/45 | 14800 (1.89) |
| Example 18 | Fluorine-containing polymer compound (13) | 33/23/17/27 | 14800 (1.99) |
| Example 19 | Fluorine-containing polymer compound (14) | 40/16/24/20 | 16400 (2.02) |
| Comparative Example 1 | Polymer compound (1) | 43/57 | 18100 (1.89) |
| Comparative Example 2 | Polymer compound (2) | 55/45 | 17800 (1.93) |
| Comparative Example 3 | Polymer compound (3) | 48/25/27 | 15100 (1.86) |
| Comparative Example 4 | Polymer compound (4) | 35/30/35 | 14500 (2.03) |
| Comparative Example 5 | Polymer compound (5) | 63/37 | 16600 (1.73) |

[Negative Resist Preparation and Pattern Formation]

A resist composition (FR-1) was prepared by dissolving the fluorine-containing polymer compound (1) into propylene glycol monomethyl ether acetate (PGMEA) in such a manner that the solid content was 14%, and then, further dissolving 5 parts by weight of triphenylsulfonium triflate (TPS 105) manufactured by Midori Kagaku Co., Ltd. as a photoacid generator, 10 parts by weight of NIKALAC MX-270 (glycoluril cross-linking agent, manufactured by Sanwa Chemical Co., Ltd.) and 0.15 parts by weight of trioctylamine as a basic compound per 100 parts by weight of the polymer compound (1). Further, resist compositions (FR-2), (FR-3), (FR-3), (FR-4), (FR-5), (FR-13), (FR-14), (R-2) and (R-3) were prepared in the same manner as above using the fluorine-containing polymer compounds (2) to (5), (18) and (19) and the polymer compounds (2) and (3), photoacid generators, cross-linking agents, basic compounds and solvents as indicated in TABLE 2. The polymer compound (1) of negative resist resin chemical structure was insoluble before exposure and thus was not subjected to pattern formation.

Each of the resist compositions was filtered with a 0.2-μm membrane filter and spin-coated on a silicon wafer substrate to form a coating film (resist film) of 300 nm thickness. The resist film was prebaked at 120° C., exposed to 248-nm ultraviolet radiation through a photomask of 200 nm size and 1-to-1 line and space (200 nm 1L/1S pattern), and then, subjected to post exposure baking treatment at 120° C. After that, the resist film was developed with 2.38 wt % aqueous tetramethylammonium hydroxide solution for 1 minute at 22° C. The negative pattern was obtained with high resolution from the resist composition (FR-2), (FR-3), (FR-3), (FR-4), (FR-5), (FR-13), (FR-14). In addition, there were seen no failures such as poor adhesion of the resist film to the substrate, poor film formation, development failure and poor etching resistance. The pattern profile of the 200 nm 1L/1S pattern resolved by the optimal exposure on the resist film was observed with a scanning electron microscope. The whole of the resist film of the resist composition (R-2) was dissolved. The pattern of the resist film of the resist composition (R-3) was distorted. The pattern profile was evaluated as "rectangular" or "distorted rectangular". The evaluation results are indicated in TABLE 2.

[Positive Resist Preparation and Pattern Formation]

A resist composition (FR-6) was prepared by dissolving the fluorine-containing polymer compound (6) into propylene glycol monomethyl ether acetate in such a manner that the solid content was 14%, and then, further dissolving 5 parts by weight of triphenylsulfonium triflate (TPS 105) manufactured by Midori Kagaku Co., Ltd. as a photoacid generator and 0.15 parts by weight of trioctylamine as a basic compound per 100 parts by weight of the polymer compound (6). Further, resist compositions (FR-7), (FR-8), (FR-9), (FR-10), (FR-11), (R-4) and (R-5) were prepared in the same manner as above using the fluorine-containing polymer compounds (7) to (11) and the polymer compounds (4) and (5), photoacid generators, cross-linking agents, basic compounds and solvents as indicated in TABLE 2.

Each of the resist compositions was filtered with a 0.2-m membrane filter and spin-coated on a silicon wafer substrate to form a coating film (resist film) of 250 nm thickness. The resist film was prebaked at 120° C., exposed to 193-nm ultraviolet radiation through a photomask of 130 nm size and 1-to-1 line and space (130 nm 1L/1S pattern), and then, subjected to post exposure baking treatment at 120° C. After that, the resist film was developed with 2.38 wt % aqueous tetramethylammonium hydroxide solution for 1 minute at 22° C.

The pattern was obtained with high resolution from the resist composition (FR-7), (FR-8), (FR-9), (FR-10), (FR-11). In addition, there were seen no failures such as poor adhesion of the resist film to the substrate, poor film formation, development failure and poor etching resistance.

The pattern profile of the 130 nm 1L/1S pattern resolved by the optimal exposure on the resist film was observed with a scanning electron microscope and evaluated as "rectangular" or "distorted rectangular". The resist film of the resist composition (R-4), (R-5) was not totally dissolved; and the pattern of the resist composition (R-4), (R-5) was unclear. The evaluation results are indicated in TABLE 2.

[Solubility Test]

A resist film was formed on a silicon wafer substrate with the application of the resist composition, prebaked at 120° C. and subjected to post exposure baking treatment at 120° C. in the same manner as above. Subsequently, the resist film was immersed in an alkali developer (2.38 wt % aqueous tetramethylammonium hydroxide solution) to examine the solubility of the resist in the alkali developer in an unexposed state.

Further, a resist film was formed on a silicon wafer substrate with the application of the resist composition, prebaked at 120° C., exposed to 248-nm ultraviolet radiation and subjected to post exposure baking treatment at 120° C. in the same manner as above. Subsequently, the resist film was immersed in an alkali developer (2.38 wt % aqueous tetramethylammonium hydroxide solution) to examine the solubility of the resist in the alkali developer after exposure. The solubility was herein examined by measuring, with an optical interference film thickness meter, a remaining part of the film after the immersion of the resist film in the alkali developer. The examination results are indicated in TABLE 2.

(Unexposed State)

The resist compositions (RF-1), (RF-2), (RF-3), (RF-4), (RF-5), (RF-5), (RF-12), (RF-13) and (RF-14) containing the fluorine-containing polymer compounds (1) to (5) and (12) to (14) according to the present invention and the resist compositions (R-2) and (R-3) containing the polymer compounds (2) and (3) according to Comparative Examples were each dissolved in the alkali developer in the unexposed state (indicated as "soluble" in TABLE 2). On the other hand, the resist compositions (RF-6), (RF-7), (RF-8), (RF-9), (RF-10) and (RF-11) containing the fluorine-containing polymer compounds (6) to (11) according to the present invention and the resist compositions (R-1), (R-4) and (R-5) containing the polymer compounds (1), (4) and (5) according to Comparative Examples were not each dissolved in the alkali developer in the unexposed state (indicated as "insoluble" in TABLE 2).

(After Exposure)

The resist compositions (RF-1), (RF-2), (RF-3), (RF-4), (RF-5), (RF-5), (RF-12), (RF-13) and (RF-14) containing the fluorine-containing polymer compounds (1) to (5) and (12) to (14) according to the present invention and the resist compositions (R-3), (R-4) and (R-5) containing the polymer compounds (3), (4) and (5) according to Comparative Examples were not each dissolved in the alkali developer after the exposure (indicated as "insoluble" in TABLE 2). On the other hand, the resist compositions (RF-6), (RF-7), (RF-8), (RF-9), (RF-10) and (RF-11) containing the fluorine-containing polymer compounds (6) to (11) according to the present invention and the resist composition (R-2) containing the polymer compound (2) according to Comparative Example were each dissolved in the alkali developer after the exposure (indicated as "soluble" in TABLE 2).

TABLE 2

| Resist | Polymer compound | Additive | Solvent | Solubility in alkali developer | | Pattern profile |
| | | | | Unexposed state | After exposure | |
| --- | --- | --- | --- | --- | --- | --- |
| FR-1 | Fluorine-containing polymer compound (1) | O-1 | S-1 | soluble | insoluble | rectangular |
| FR-2 | Fluorine containing polymer compound (2) | O-1 | S-1 | soluble | insoluble | rectangular |
| FR-3 | Fluorine-containing polymer compound (3) | O-1 | S-2 | soluble | insoluble | rectangular |
| FR-4 | Fluorine-containing polymer compound (4) | O-2 | S-1 | soluble | insoluble | rectangular |
| FR-5 | Fluorine-containing polymer compound (5) | O-1 | S-1 | soluble | insoluble | rectangular |
| FR-6 | Fluorine-containing polymer compound (6) | O-1 | S-2 | insoluble | soluble | rectangular |
| FR-7 | Fluorine-containing polymer compound (7) | O-1 | S-1 | insoluble | soluble | rectangular |
| FR-8 | Fluorine containing polymer compound (8) | O-1 | S-1 | insoluble | soluble | rectangular |
| FR-9 | Fluorine-containing polymer compound (9) | O-1 | S-1 | insoluble | soluble | rectangular |
| FR-10 | Fluorine-containing polymer compound (10) | O-2 | S-2 | insoluble | soluble | rectangular |
| FR-11 | Fluorine-containing polymer compound (11) | O-2 | S-1 | insoluble | soluble | rectangular |
| FR-12 | Fluorine-containing polymer compound (12) | O-1 | S-1 | soluble | insoluble | rectangular |
| FR-13 | Fluorine-containing polymer compound (13) | O-1 | S-1 | soluble | insoluble | rectangular |
| FR-14 | Fluorine containing polymer compound (14) | O-1 | S-1 | soluble | insoluble | rectangular |
| R-1 | Polymer compound (1) | O-1 | S-1 | — | — | — |
| R-2 | Polymer compound (2) | O-1 | S-1 | soluble | soluble | — |
| R-3 | Polymer compound (3) | O-1 | S-1 | soluble | insoluble | distorted rectangular |
| R-4 | Polymer compound (4) | O-1 | S-1 | insoluble | insoluble | — |
| R-5 | Polymer compound (5) | O-1 | S-1 | insoluble | insoluble | — |

Resin: 14 parts by weight
Photoacid generator: triphenylsulfonium triflate (TPS 105) manufactured by Midori Kagaku Co., Ltd., 5 parts by weight
Basic compound: O-1 (trioctylamine), O-2 (diazabicyclo [4.3.0]nonene), 0.15 parts by weight
Cross-linking agent: NIKALAC MX-270 (glycoluril cross-linking agent, manufactured by Sanwa Chemical Co., Ltd.), 10 parts by weight
Solvent: S-1 (PGMEA), S-2 (γ-butyrolactone), 86 parts by weight

INDUSTRIAL APPLICABILITY

The fluorine-containing polymer compound of the present invention is useful for the resist composition.

The invention claimed is:

1. A fluorine-containing unsaturated carboxylic acid amide of the following general formula (1)

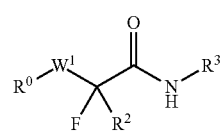

(1)

where $R^0$ represents any of polymerizable double bond-containing groups of the following formulas:

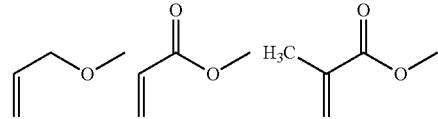

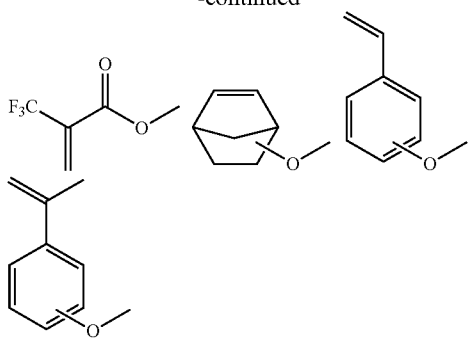

$R^2$ represents a fluorine atom or a fluorine-containing alkyl group;

$R^3$ represents a hydrogen atom, a substituted or unsubstituted $C_1$-$C_{20}$ straight, branched or cyclic alkyl group or a substituted or unsubstituted $C_3$-$C_{20}$ aryl group, each of carbon atoms of the alkyl group or the aryl group may be replaced by a carbonyl group, an oxygen atom, a sulfur atom or a silicon atom, each of hydrogen atoms of the alkyl group or the aryl group may be replaced by a halogen atom;

$W^1$ represents a divalent linking moiety constituted by combination of one or two or more organic groups each selected from the group consisting of a single bond, a substituted or unsubstituted methylene group, a divalent alicyclic hydrocarbon group, a divalent aromatic hydrocarbon group, a divalent heterocyclic group, an ether group, a carbonyl group, an ester group, an oxocarbonyl group, a thioether group, an amide group, a sulfonamide group, an urethane group and an urea group; when the linking moiety contains a plurality of organic groups, the organic groups can be of the same kind; an arbitrary number of hydrogen atoms bonded to any carbon atom of the linking moiety may be substituted with a fluorine atom; and carbon atoms of the linking moiety may form a ring with a substituent.

2. The fluorine-containing unsaturated carboxylic acid amide according to claim 1, wherein $R^2$ is a fluorine atom.

3. The fluorine-containing unsaturated carboxylic acid amide according to claim 1, wherein $R^3$ is a hydrogen atom.

4. The fluorine-containing unsaturated carboxylic acid amide according to claim 1, wherein $R^3$ is an acid labile group.

5. The fluorine-containing unsaturated carboxylic acid amide according to claim 1, wherein $R^3$ is a neutral alkoxyl-containing group.

6. A fluorine-containing polymer compound, comprising a repeating unit (a) of the following general formula (2) and having a weight-average molecular weight of 1000 to 1000000

(2)

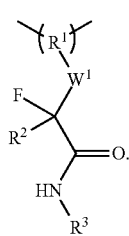

where $R^1$ represents a group formed by cleavage of a polymerizable double bond of $R^0$ defined in the general formula (1) of claim 1; and $R^2$, $R^3$ and $W^1$ are the same as defined in the general formula (1).

7. The fluorine-containing polymer compound according to claim 6, wherein $R^2$ is a fluorine atom.

8. The fluorine-containing polymer compound according to claim 6, wherein $R^3$ is a hydrogen atom.

9. The fluorine-containing polymer compound according to claim 6, wherein $R^3$ is an acid labile group.

10. The fluorine-containing polymer compound according to claim 6, wherein $R^3$ is a neutral alkoxyl-containing group.

11. The fluorine-containing polymer compound according to claim 6, further comprising a repeating unit (b) formed by cleavage of a polymerizable double bond of a copolymerizable monomer selected from the group consisting of acrylic esters, fluorine-containing acrylic esters, methacrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylic amides, methacrylic amides, vinyl esters, allyl esters, olefins, fluorine-containing olefins, norbornene compounds, fluorine-containing norbornene compounds, sulfur dioxide and vinyl silanes.

12. The fluorine-containing polymer compound according to claim 11, wherein the repeating unit (b) has a lactone ring.

13. A resist composition, comprising at least the fluorine-containing polymer compound according to claim 6 and a solvent.

14. The resist composition according to claim 13, wherein the resist composition further comprises a photoacid generator and functions as a chemically amplified resist composition.

15. The resist composition according to claim 14, wherein the resist composition functions as a chemically amplified positive resist composition.

16. The resist composition according to claim 14, wherein the resist composition further comprises a cross-linking agent and functions as chemically amplified negative resist composition.

17. A pattern formation method, comprising at least:
applying a film of the resist composition according to claim 13 to a substrate;
heat-treating the substrate with the film of the resist composition being applied;
exposing the film of the resist composition to high energy radiation of 300 nm or less wavelength or electron beam radiation through a photomask;
heat-treating the exposed film of the resist composition; and
developing the heat-treated, exposed film of the resist composition with a developer.

18. The pattern formation method according to claim 17, wherein the high energy radiation is either near-ultraviolet radiation, vacuum ultraviolet radiation (VUV), extreme ultraviolet radiation (EUV) or soft X-ray radiation.

19. The fluorine-containing unsaturated carboxylic acid amide according to claim 1, wherein, in the general formula (1), $R^0$ represents an acryloxy group, a methacryloxy group, a trifluoromethacryloxy group, or an allyloxy group.

* * * * *